United States Patent [19]

Al-Razzak et al.

[11] Patent Number: 5,484,801

[45] Date of Patent: Jan. 16, 1996

[54] PHARMACEUTICAL COMPOSITION FOR INHIBITING HIV PROTEASE

[75] Inventors: Laman A. Al-Razzak, Libertyville; Kennan C. Marsh, Lake Forest; Lourdes P. Manning, Grayslake; Dilip Kaul, Waukegan, all of Ill.

[73] Assignee: Abbott Laboratories, Abbott Park, Ill.

[21] Appl. No.: 440,277

[22] Filed: May 12, 1995

Related U.S. Application Data

[63] Continuation of Ser. No. 283,239, Jul. 29, 1994, abandoned, which is a continuation-in-part of Ser. No. 189,021, Jan. 28, 1994, abandoned.

[51] Int. Cl.$^6$ ............... C07D 277/30; A61K 31/425; A01N 43/78
[52] U.S. Cl. ............ 514/365; 514/885; 514/974; 548/204
[58] Field of Search .................. 514/885, 365, 514/974; 548/204

[56] References Cited

U.S. PATENT DOCUMENTS

| | | | |
|---|---|---|---|
| 5,086,165 | 2/1992 | Marshall et al. | 530/329 |
| 5,164,300 | 11/1992 | Marshall et al. | 435/23 |
| 5,171,662 | 12/1992 | Sharma | 435/5 |
| 5,183,826 | 2/1993 | Bills et al. | 514/411 |
| 5,250,563 | 10/1993 | Chen et al. | 514/411 |
| 5,256,677 | 10/1993 | Sham et al. | 514/351 |
| 5,296,604 | 3/1994 | Hanko et al. | 548/169 |
| 5,342,922 | 8/1994 | Marshall et al. | 530/329 |
| 5,354,866 | 10/1994 | Kempf et al. | 546/265 |

FOREIGN PATENT DOCUMENTS

| | | |
|---|---|---|
| 486948 | 5/1992 | European Pat. Off. . |
| WO92/00750 | 1/1992 | WIPO . |
| WO94/14436 | 7/1994 | WIPO . |

*Primary Examiner*—Ronald W. Griffin
*Attorney, Agent, or Firm*—Steven R. Crowley

[57] ABSTRACT

A pharmaceutical composition is disclosed which comprises a solution of an HIV protease inhibiting compound in a pharmaceutically acceptable organic solvent comprising a mixture of (1) (a) a solvent selected from propylene glycol and polyethylene glycol or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy)ethanol or (c) a mixture thereof and (2) ethanol or propylene glycol.

28 Claims, No Drawings

5,484,801

PHARMACEUTICAL COMPOSITION FOR INHIBITING HIV PROTEASE

This is a continuation of U.S. patent application Ser. No. 283,239, filed Jul. 29, 1994, now abandoned, which is a continuation-in-part of U.S. patent application Ser. No. 189,021, filed Jan. 28, 1994, now abandoned.

TECHNICAL FIELD

A liquid pharmaceutical composition providing improved oral bioavailability is disclosed for compounds which are inhibitors of HIV protease (in particular, HIV-1 and HIV-2 protease). In particular, the composition comprises the HIV protease inhibitor and one or more pharmaceutically acceptable organic solvents.

BACKGROUND OF THE INVENTION

One measure of the potential usefulness of an oral dosage form of a new pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the aqueous oral solution formulation of a drug is then generally used as the standard or ideal bioavailability against which other oral dosage forms are measured.

It has recently been determined that HIV protease inhibiting compounds are useful for inhibiting HIV protease in vitro and in vivo and are useful-for inhibiting an HIV (human immunodeficiency virus) infection and are useful for treating AIDS (acquired immunodeficiency syndrome). HIV protease inhibiting compounds typically are characterized by having poor oral bioavailability.

Examples of HIV protease inhibiting compounds include N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide and related compounds, disclosed in European Patent Application No. EP541168, published May 12, 1993;

N-tert-butyl-decahydro-2-[2(R)-hydroxy-4-phenyl-3(S)-[ [N-(2-quinolylcarbonyl)-L-asparaginyl]amino] butyl]-(4aS,8aS)-isoquinoline-3(S)-carboxamide and related compounds, disclosed in U.S. Pat. No. 5,196,438, issued Mar. 23, 1993;

[1S-[1R*(R*),2S*]]-$N^1$[3-[[[(1,1-dimethylethyl)amino] carbonyl](2 -methylpropyl)amino]-2-hydroxy-1-(phenylmethyl)propyl]-2-[(2 -quinolinylcarbonyl)amino]-butanediamide and related compounds, disclosed in PCT Patent Application No. WO92/08701, published May 29, 1992; and

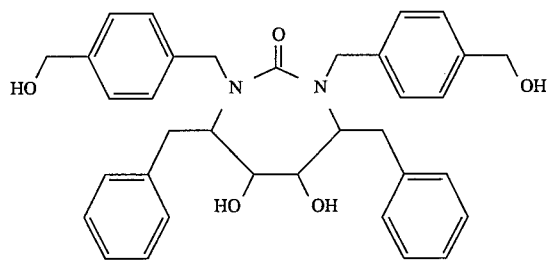

and related compounds,, disclosed in PCT Patent Application No. WO93/07128, published Apr. 15, 1993.

It has recently been determined that compounds of the formula I:

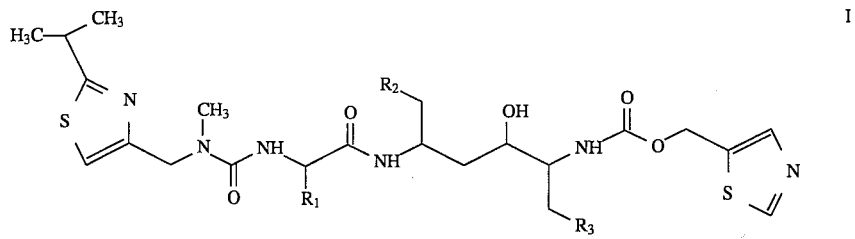

wherein $R_1$ is lower alkyl and $R_2$ and $R_3$ are phenyl are inhibitors of HIV-1 and HIV-2 protease and are useful for inhibiting HIV protease in vitro and in vivo and are useful to inhibit HIV (human immunodeficiency virus) infections and, thus, are useful for the treatment of AIDS (acquired immunodeficiency syndrome).

In particular, the compound of formula II, has been found to be especially effective as an inhibitor of HIV-1 and HIV-2 protease.

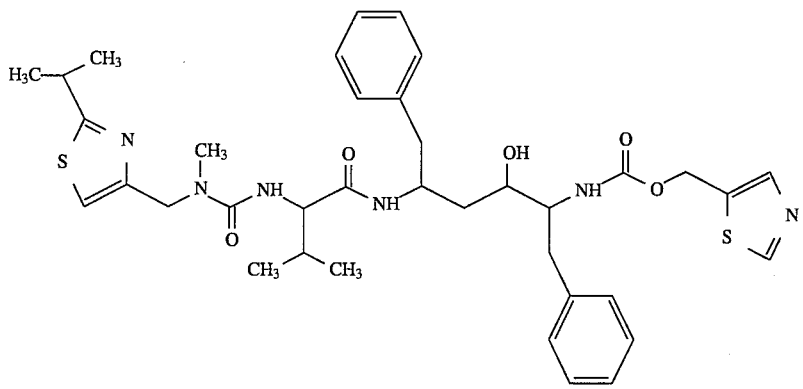

The most preferred compound of formula II is (2S,3S, 5S)-5-(N-(N-((N-Methyl-N-((2-isopropyl-4-thiazolyl)m-ethyl)-amino)carbonyl)valinyl)amino )-2-(N-((5-thiazolyl)methoxycarbonyl)amino)-1,6-diphenyl-3-hydroxyhexane (compound III).

Compound III has an aqueous solubility of approximately 6 micrograms per milliliter at pH>2. This is considered to be extremely poor aqueous solubility and, therefore, compound III in the free base form would be expected to provide very low oral bioavailability. In fact, the free base form of compound III, administered as an unformulated solid in a capsule dosage form, is characterized by a bioavailability of less than 2% following a 5 mg/kg oral dose in dogs.

Acid addition salts of compound III (for example, bis-hydrochloride, bis-tosylate, bis-methane sulfonate and the like) have aqueous solubilities of <0.1 milligrams/milliliter. This is only a slight improvement over the solubility of the free base. This low aqueous solubility would not make practical the administration of therapeutic amounts of compound III as an aqueous solution. Furthermore, in view of this low aqueous solubility, it is not surprising that the bis-tosylate of compound III, administered as an unformulated solid in a capsule dosage form, is characterized by a bioavailability of less than 2% following a 5 mg/kg oral dose in dogs.

In order to have a suitable oral dosage form of compound III, the oral bioavailability of compound III should be at least 20%. Preferably, the oral bioavailability of compound III from the dosage form should be greater than about 40% and, more preferably, greater than about 50%.

While some drugs would be expected to have good solubility in organic solvents, it would not necessarily follow that oral administration of such an organic solution would give good bioavailability for the drug. It has been found that compound III has good solubility in pharmaceutically acceptable organic solvents. In addition, the solubility of compound III in some organic solvents is enhanced in the presence of a pharmaceutically acceptable acid. Unexpectedly, solutions of compound III in pharmaceutically acceptable organic solvents provide an oral bioavailability of from about 40% to about 100% in dogs.

DISCLOSURE OF THE INVENTION

In accordance with the present invention, there is a pharmaceutical composition comprising a solution of an HIV protease inhibiting compound (preferably, a compound of the formula II) in a pharmaceutically acceptable organic solvent comprising a mixture of (1) (a) a solvent selected from propylene glycol and polyethylene glycol or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy)ethanol or (c) a mixture thereof and (2) ethanol or propylene glycol.

A preferred composition of the invention comprises a solution of an HIV protease inhibiting compound (preferably, a compound of the formula II) in a pharmaceutically acceptable organic solvent comprising a mixture of (1) propylene glycol or polyoxyethyleneglycerol triricinoleate or a mixture thereof and (2) ethanol.

The solution composition of the invention can also comprise other pharmaceutically acceptable organic solvents.

The solution composition of the invention can also comprise from about 0% to about 20% (preferably, from about 0.2% to about 16% and more preferably from about 0.2% to about 6%, by weight of the total solution) of a pharmaceutically acceptable acid or a mixture of pharmaceutically acceptable acids.

The solution composition of the invention can also comprise from about 0% to about 25% (preferably, from about 0% to about 19%, by weight of the total solution) of water.

The solution composition of the invention can also comprise one or more pharmaceutically acceptable oils.

The solution of the invention can also comprise pharmaceutically acceptable sweetening agents and/or pharmaceutically acceptable flavoring agents (for example, sucrose, aspartame, sorbitol, saccharin sodium and the like and/or cherry flavor, artificial banana flavor, caramel, chocolate mint flavor, grape flavor, wild cherry flavor, raspberry flavor, strawberry flavor, citrus flavor, orange flavor, pineapple flavor, citrus lime flavor, citrus cream flavor, cherry vanilla flavor, creme de menthe flavor and the like).

In addition, the solution composition of the invention can comprise one or more pharmaceutically acceptable surfactants.

In addition, the solution composition of the invention can comprise antioxidants (for example, ascorbic acid, BHA (butylated hydroxyanisole), BHT (butylated hydroxytoluene), vitamin E, vitamin E PEG 1000 succinate and the like) for chemical stability.

The compositions of this invention provide improved oral bioavailability for compound II when compared to non-formulated compound II (base) or non-formulated compound II (acid addition salt), or even when compared to a mixed aqueous/organic solution (50% water, 20% ethanol, 30% propylene glycol) of compound II (methansulfonate acid addition salt).

The term "pharmaceutically acceptable organic solvent" as used herein refers to propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); fractionated coconut oil (for example, mixed triglycerides with caprylic acid and capric acid (Miglyol®812, available from Huls AG, Witten, Germany) and the like); Tween®80; isopropyl palmitate; isopropyl myristate; pharmaceutically acceptable silicon fluids; and the like.

The term "pharmaceutically acceptable acid" as used herein refers to (i) an inorganic acid such as hydrochloric acid, hydrobromic acid, hydroiodic acid and the like, (ii) an organic mono-, di- or tri-carboxylic acid (for example, formic acid, acetic acid, adipic acid, alginic acid, citric acid, ascorbic acid, aspartic acid, benzoic acid, butyric acid, camphoric acid, gluconic acid, glucuronic acid, galactaronic acid, glutamic acid, heptanoic acid, hexanoic acid, fumaric acid, lactic acid, lactobionic acid, malonic acid, maleic acid, nicotinic acid, oxalic acid, pamoic acid, pectinic acid, 3-phenylpropionic acid, picric acid, pivalic acid, propionic acid, succinic acid, tartaric acid, undecanoic acid and the like) or (iii) a sulfonic acid (for example, benzenesulfonic acid, sodium bisulfate, sulfuric acid, camphorsulfonic acid, dodecylsulfonic acid, ethanesulfonic acid, methanesulfonic acid, isethionic acid, naphthalenesulfonic acid, p-toluenesulfonic acid and the like).

The term "pharmaceutically acceptable oil" as used herein refers to mineral oil or a vegetable oil (for example, safflower oil, peanut oil, olive oil, fractionated coconut oil (for example, mixed triglycerides with caprylic acid and capric acid (Miglyol®812, available from Huls AG, Witten, Germany) and the like).

The term "pharmaceutically acceptable surfactant" as used herein refers to a pharmaceutically acceptable non-ionic surfactant (for example, polyethylenepolypropylene glycol, such as Poloxamer®68 (BASF Wyandotte Corp.) or a mono fatty acid ester of polyoxyethylene (20) sorbitan (for example, polyoxyethylene (20) sorbitan monooleate (Tween®80), polyoxyethylene (20) sorbitan monostearate (Tween®60), polyoxyethylene (20) sorbitan monopalmitate (Tween®40), polyoxyethylene (20) sorbitan monolaurate (Tween®20) and the like) and the like) or a pharmaceutically acceptable anionic surfactant (for example, sodium lauryl sulfate and the like).

A preferred composition of the invention comprises an HIV protease inhibiting compound (preferably, a compound of the formula II) in the amount of from about 1% to about 15% by weight of the total solution (more preferably, from about 2.5% to about 10% by weight of the total solution) in a pharmaceutically acceptable organic solvent comprising a mixture of (1) (a) a solvent selected from propylene glycol and polyethylene glycol in the amount of from about 10% to about 50% by weight of the total solution or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy)ethanol in the amount of from about 5% to about 35% by weight of the total solution or (c) a mixture thereof and (2) ethanol or propylene glycol in the amount of from about 5% to about 45% by weight of the total solution (more preferably, from about 20% to about 35% by weight of the total solution).

Preferably, in the composition of the invention, the mixture of pharmaceutically acceptable organic solvents (including ethanol) comprises from about 50% to about 95% by weight of the total solution. More preferably, the mixture of pharmaceutically acceptable organic solvents comprises from about 70% to about 95% by weight of the total solution.

In the composition of the invention, another preferred mixture of pharmaceutically acceptable solvents is a mixture of propylene glycol (about 42% by weight of the total solution), ethanol (about 32% by weight of the total solution) and water (from about 16% to about 17% by weight of the total solution).

In the composition of the invention, a preferred mixture of pharmaceutically acceptable solvents is a mixture of propylene glycol (about 32% by weight of the total solution), ethanol (about 37% by weight of the total solution) and water (about 15% by weight of the total solution).

In the composition of the invention, another preferred mixture of pharmaceutically acceptable solvents is a mixture of propylene glycol (from about 44% to about 45% by weight of the total solution), polyoxyethyleneglycerol triricinoleate (about 20% by weight of the total solution) and ethanol (from about 24% to about 25% by weight of the total solution).

In the composition of the invention, another preferred mixture of pharmaceutically acceptable solvents is a mixture of propylene glycol (from about 39% to about 40% by weight of the total solution), polyoxyethyleneglycerol triricinoleate (about 20% by weight of the total solution) and ethanol (about 24% by weight of the total solution).

In the composition of the invention, another preferred mixture of pharmaceutically acceptable solvents is a mixture of propylene glycol (about 43% by weight of the total solution), ethanol (about 33% by weight of the total solution) and water (about 17% by weight of the total solution).

In the composition of the invention, another preferred mixture of pharmaceutically acceptable solvents is a mixture of propylene glycol (about 36% by weight of the total solution), ethanol (about 36% by weight of the total solution) and water (about 19% by weight of the total solution).

In the composition of the invention, another preferred mixture of pharmaceutically acceptable solvents is a mixture of propylene glycol (about 35% by weight of the total solution), ethanol (about 35% by weight of the total solution) and water (about 18% by weight of the total solution).

In the composition of the invention, another preferred mixture of pharmaceutically acceptable solvents is a mixture of propylene glycol (about 31% by weight of the total solution), polyoxyethyleneglycerol triricinoleate (about 10% by weight of the total solution), ethanol (about 32% by weight of the total solution) and water (about 14% by weight of the total solution).

In the composition of the invention, another preferred mixture of pharmaceutically acceptable solvents is a mixture of propylene glycol (about 46% by weight of the total solution), ethanol (about 21% by weight of the total solution) and polyoxyethyleneglycerol triricinoleate (about 24% by weight of the total solution).

A preferred pharmaceutically acceptable acid is citric acid.

A most preferred composition of the invention comprises a solution of a compound of the formula III in the amount of from about 1% to about 15% by weight of the total solution (more preferably, from about 2.5% to about 12% by weight of the total solution) in a pharmaceutically acceptable organic solvent comprising a mixture of (1) propylene glycol or polyoxyethyleneglycerol triricinoleate or a mixture thereof and (2) ethanol.

In the most preferred composition of the invention, the preferred pharmaceutically acceptable solvents and acids are as described above for the preferred composition of the invention.

An even more preferred composition of the invention comprises a solution of a compound of the formula III in the amount of from about 5% to about 8% by weight of the total solution in a pharmaceutically acceptable organic solvent comprising a mixture of (1) propylene glycol in the amount of from about 34% to about 36% by weight of the total solution, (2) ethanol in the amount of from about 34% to about 36% by weight of the total solution and (3) water in the amount of from about 18% to about 19% by weight of the total solution. The even more preferred composition also comprises citric acid in the amount of from about 0.3% to about 0.4% by weight of the total solution:

Another even more preferred composition of the invention comprises a solution of a compound of the formula III in the amount of from about 7% to about 8% by weight of the total solution in a pharmaceutically acceptable organic solvent comprising a mixture of (1) propylene glycol in the amount of from about 45% to about 46% by weight of the total solution, (2) ethanol in the amount of about 21% by weight of the total solution and (3) polyoxyethyleneglycerol triricinoleate in the amount of from about 24% to about 25% by weight of the total solution. The even more preferred composition also comprises citric acid in the amount of about 0.5% by weight of the total solution.

A most highly preferred composition of the invention comprises a solution of a compound of the formula III in the amount of from about 7% to about 8% by weight of the total solution in a pharmaceutically acceptable organic solvent comprising a mixture of (1) propylene glycol in the amount of from about 31% to about 32% by weight of the total solution, (2) ethanol in the amount of about 32% by weight of the total solution, (3) polyoxyethyleneglycerol triricinoleate in the amount of from about 10% to about 11% by weight of the total solution and (4) water in the amount of from about 14% to about 15% by weight of the total solution. The even more preferred composition also comprises citric acid in the amount of from about 0.2% to about 0.3% by weight of the total solution.

The compounds of formula 1 and II contain two or more asymmetric carbon atoms and thus can exist as pure diastereomers, mixtures of diastereomers, diastereomeric racemates or mixtures of diastereomeric racemates. The present invention is intended to include within its scope all of the isomeric forms. The terms "R" and "S" configuration as used herein are as defined by IUPAC 1974 Recommendations for Section E, Fundamental Stereochemistry, Pure Appl. Chem. (1976) 45, 13–30.

The preferred isomer of the compound of formula II is (2S,3S,5S)-5-(N-(N-((N-Methyl-N-((-2-isopropyl-4-thiazolyl)methyl)-amino)carbonyl)valinyl)amino)-2-(N-((5-thiazolyl)methoxycarbonyl)amino)-1,6-diphenyl-3-hydroxyhexane (compound III).

The term "lower alkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

In general, the compositions of this invention can be prepared in the following manner. The ethanol and the pharmaceutically acceptable acid (if present) and the water (if present) and sweetener (if present) are mixed. To this solution is added the propylene glycol or polyethylene glycol and/or polyoxyethyleneglycerol triricinoleate, polyethylene glycol 40 hydrogenated castor oil, fractionated coconut oil, polyoxyethylene (20) sorbitan monooleate or 2-(2-ethoxyethoxy)ethanol until the resulting solution is clear. Compound III (along with any other solvents, oils or other additives) are added to the solution and mixed until the solution is clear. The resulting solution is brought to the desired final volume with the addition of propylene glycol or polyethylene glycol and/or polyoxyethyleneglycerol triricinoleate, polyethylene glycol 40 hydrogenated castor oil, fractionated coconut oil, polyoxyethylene (20) sorbitan monooleate or 2-(2-ethoxyethoxy)ethanol.

Alternatively, the ethanol and pharmaceutically acceptable acid (if present) are mixed, followed by addition of compound III. To this mixture is added the propylene glycol or polyethylene glycol and/or polyoxyethyleneglycerol triricinoleate, polyethylene glycol 40 hydrogenated castor oil, fractionated coconut oil, polyoxyethylene (20) sorbitan monooleate or 2-(2-ethoxyethoxy)ethanol until the resulting solution is clear. Then the water (if present) and sweetener (if present), along with any other solvents, oils or other additives, are added with mixing until the solution is clear. The resulting solution is brought to the desired final volume with the addition of propylene glycol or polyethylene glycol and/or polyoxyethyleneglycerol triricinoleate, polyethylene glycol 40 hydrogenated castor oil, fractionated coconut oil, polyoxyethylene (20) sorbitan monooleate or 2-(2-ethoxyethoxy)ethanol.

The following examples will serve to further illustrate the invention. In particular, Examples 5–19 relate specifically to this invention.

EXAMPLE 1

(non-formulated capsule)

An amount of compound III (free base) equivalent to a 5 mg/kg dose was placed in hard gelatin capsules (gray, size 0). These capsules were administered to fasted dogs with 10 ml of water.

EXAMPLE 2

(Capsule)

An amount of compound III (free base) equivalent to a 5 mg/kg dose was placed in hard gelatin capsules (gray, size 0). These capsules were administered to non-fasted dogs with ten milliliter of water.

EXAMPLE 3

(Capsule)

An amount of the bis-tosylate salt of compound III equivalent to a 5 mg/kg dose of compound III (base equivalent) was filled into hard gelatin capsules (gray, size 0). These capsules were administered to nonfasted dogs with ten milliliter of water.

EXAMPLE 4

(Solution)

A 5 mg (free base equivalent)/ml solution of the base compound III in 20% ethanol: 30% propylene glycol: dextrose containing 2- molar equivalents of methane sulfonic acid.

| Component | % By Weight |
| --- | --- |
| Compound III (free base) | 0.5 |
| Propylene glycol (Aldrich, reagent) | 31.9 |
| Ethanol (USP, 200 proof) | 16.2 |
| methanesulfonic acid (Aldrich reagent) | 0.14 |
| Dextrose | 3.6 |
| Water for injection (USP) | 47.6 |

EXAMPLE 5

A 50 mg/ml solution of the base compound III.

| Component | % By Weight |
| --- | --- |
| Compound III (free base) | 5.1 |
| Propylene glycol (USP) | 42.22 |
| Ethanol (USP, 200 proof, dehydrated) | 32.21 |
| Citric acid (USP, anhydrous, powder) | 3.93 |
| Water for injection (USP) | 16.54 |

Citric acid (77.0 g) was mixed with water (300 mL) and stirred until the solution was clear. Water was added to bring the volume of solution to 400 mL. Propylene glycol (300 g) and ethanol (800 g) were mixed in a stainless steel beaker until the solution was clear. To the propylene glycol/ethanol solution was added compound III (100.4 g) with stirring and mixing was continued until the solution was clear. To this solution was added the citric acid solution until the final volume was 2000 mL.

If a flavoring agent is to be included, it would be added to the solution of compound III prior to addition of the citric acid solution.

EXAMPLE 6

A 25 mg/ml solution of the base compound III.

| Component | % By Weight |
| --- | --- |
| Compound III (free base) | 2.6 |
| Propylene glycol (USP) | 43.4 |
| Ethanol (USP, 200 proof, dehydrated) | 33.04 |
| Citric acid (USP, anhydrous, powder) | 4.0 |
| Water for injection (USP) | 16.95 |

EXAMPLE 7

A 50 mg/ml solution of the base compound III.

| Component | % By Weight |
| --- | --- |
| Compound III (free base) | 5.37 |
| Propylene glycol (USP) | 28.85 |
| Ethanol (USP, 200 proof, dehydrated) | 43.35 |
| Citric acid (USP, anhydrous, powder) | 4.3 |
| Water for injection (USP) | 18.14 |

EXAMPLE 8

A 50 mg/ml solution of the base compound III.

| Component | % By Weight |
| --- | --- |
| Compound III (free base) | 5.3 |
| Propylene glycol (USP) | 31 |
| Ethanol (USP, 200 proof, dehydrated) | 42.1 |
| Citric acid (USP, anhydrous, powder) | 3.8 |
| Water for injection (USP) | 16.05 |
| Aspartame | 1.60 |
| Wild cherry flavor | 0.14 |

EXAMPLE 9

A 50 mg/ml solution of the base compound III.

| Component | % By Weight |
| --- | --- |
| Compound III (free base) | 5.39 |
| Cremophor ® EL (polyoxyl 35 castor oil, NF) | 32.18 |
| Ethanol (USP, 200 proof, dehydrated) | 32.3 |
| Miglyol ® 812 | 30.13 |

EXAMPLE 10

A 50 mg/ml solution of the base compound III.

| Component | % By Weight |
| --- | --- |
| Compound III (free base) | 5.01 |
| Propylene glycol (USP) | 44.6 |
| Ethanol (USP, 200 proof, dehydrated) | 24.53 |
| Citric acid (USP, anhydrous, powder) | 5.76 |
| Cremophor ® EL (polyoxyl 35 castor oil, NF) | 20.1 |

EXAMPLE 11

A 50 mg/ml solution of the base compound III.

| Component | % By Weight |
| --- | --- |
| Compound III (free base) | 5.04 |
| Propylene glycol (USP) | 44.39 |
| Ethanol (USP, 200 proof, dehydrated) | 24.42 |
| Citric acid (USP, anhydrous, powder) | 5.82 |
| Cremophor ® EL (polyoxyl 35 castor oil, NF) | 20.33 |

Citric acid (153.6 g) and ethanol (800 mL) were mixed until the solution was clear. To this solution was added with mixing polyoxyl 35 castor oil (400 g) and enough propylene glycol until the solution was clear. Compound III (100 g) was added with mixing until the solution was clear. Propylene glycol was added to bring the final volume of the solution to 2000 mL.

Alternatively, citric acid (153.6 g) and ethanol (800 mL) were mixed until the solution was clear. Compound III (100 g) was added with mixing until the solution was clear. To this solution was added with mixing polyoxyl 35 castor oil (400 g) and enough propylene glycol until the solution was clear. Propylene glycol was added to bring the final volume of the solution to 2000 mL.

EXAMPLE 12

A 50 mg/ml solution of the base compound III.

| Component | % By Weight |
|---|---|
| Compound III (free base) | 5.11 |
| Propylene glycol (USP) | 24.05 |
| Ethanol (USP, 200 proof, dehydrated) | 20.29 |
| Cremophor ® EL (polyoxyl 35 castor oil, NF) | 35.59 |
| Miglyol ® 812 | 5.0 |
| Tween ® 80 | 9.97 |

EXAMPLE 13

A 100 mg/ml solution of the base compound III.

| Component | % By Weight |
|---|---|
| Compound III (free base) | 10.05 |
| Propylene glycol (USP) | 39.64 |
| Ethanol (USP, 200 proof, dehydrated) | 24.3 |
| Cremophor ® EL (polyoxyl 35 castor oil, NF) | 20.23 |
| Citric acid (USP, anhydrous, powder) | 5.76 |

EXAMPLE 14

A 100 mg/ml solution of the base compound III.

| Component | % By Weight |
|---|---|
| Compound III (free base) | 4.99 |
| Propylene glycol (USP) | 43.52 |
| Ethanol (USP, 200 proof, dehydrated) | 24.2 |
| Cremophor ® EL (polyoxyl 35 castor oil, NF) | 19.96 |
| Citric acid (USP, anhydrous, powder) | 5.76 |
| Banana flavor | 0.5 |
| Strawberry flavor | 0.59 |
| Sodium saccharin | 0.5 |

EXAMPLE 15

A 130 mg/ml solution of the base compound III.

| Component | % By Weight |
|---|---|
| Compound III (free base) | 12.0 |
| Propylene glycol (USP) | 32.4 |
| Ethanol (USP, 200 proof, dehydrated) | 37.0 |
| Citric acid (USP, anhydrous, powder) | 3.6 |
| Water for injection (USP) | 15.0 |

EXAMPLE 16

A 50 mg/ml solution of the base compound III.

| Component | % By Weight |
|---|---|
| Compound III (free base) | 5.125 |
| Propylene glycol (USP) | 35.8 |
| Ethanol (USP, 200 proof, dehydrated) | 35.75 |
| Citric acid (USP, anhydrous, powder) | 0.362 |
| Water for injection (USP) | 18.86 |
| Sodium Saccharin (USP, powder, dihydrate) | 1.02 |
| Wild cherry flavor, artificial | 3.0 |
| Flavor enhancer (Prosweet ® Liquid "K") | 0.08 |
| (Prosweet ® Liquid "K" is available from Virginia Dare, 882 Third Ave., Brooklyn, NY) | |
| Dye, Red D&C No. 33 | 0.01 |

EXAMPLE 17

A 80 mg/ml solution of the base compound III.

| Component | % By Weight |
|---|---|
| Compound III (free base) | 7.96 |
| Propylene glycol (USP) | 34.72 |
| Ethanol (USP, 200 proof, dehydrated) | 34.7 |
| Citric acid (USP, anhydrous, powder) | 0.35 |
| Water for injection (USP) | 18.3 |
| Sodium Saccharin (USP, powder, dihydrate) | 0.99 |
| Wild cherry flavor, artificial | 2.9 |
| Flavor enhancer (Prosweet ® Liquid "K") | 0.08 |
| Dye, Red D&C No. 33 | 0.01 |

EXAMPLE 18

An 80 mg/ml solution of the base compound III.

| Component | % By Weight |
|---|---|
| Compound III (free base) | 7.88 |
| Propylene glycol (USP) | 31.31 |
| Ethanol (USP, 200 proof, dehydrated) | 32.0 |
| Citric acid (USP, anhydrous, powder) | 0.27 |
| Water for injection (USP) | 14.18 |
| Cremophor ® EL | 10.4 |
| Sodium Saccharin (USP, powder, dihydrate) | 0.98 |
| Wild cherry flavor, artificial | 2.875 |
| Flavor enhancer (Prosweet ® Liquid "K") | 0.08 |
| Dye, Red D&C No. 33 | 0.01 |

The water (14.4 mL) and ethanol (41.2 mL) were mixed and the citric acid (276 mg) was added with stirring. The sodium saccharin (1.0 g), flavor enhancer (0.1 mL), propylene glycol (30.7 mL), compound III (8.0 g), red dye (10.0 mg), and cherry flavor (3.7 mL) were added sequentially with stirring. The resulting solution was brought to a final volume of 100 mL by addition of the Cremophor® EL. The final solution was stored at 2°–8° C. until it was filled into 15 mL vials.

EXAMPLE 19

An 80 mg/ml solution of the base compound III.

| Component | % By Weight |
|---|---|
| Compound III (free base) | 7.57 |
| Propylene glycol (USP) | 45.7 |

-continued

| Component | % By Weight |
|---|---|
| Ethanol (USP, 200 proof, dehydrated) | 21.0 |
| Citric acid (USP, anhydrous, powder) | 0.51 |
| Cremophor ® EL | 24.29 |
| Sodium Saccharin (USP, powder, dihydrate) | 0.47 |
| Flavor enhancer (Prosweet ® Liquid "K") | 0.148 |
| Flavor, chocolate mint | 0.37 |

The ethanol (28.4 mL) were mixed and the citric acid (545 mg) was added with stirring. Enough of the propylene glycol was added with stirring to make the resulting solution clear. The sodium saccharin (500 mg), flavor enhancer (0.2 mL), compound III (8.0 g), Cremophor® EL (24.5 mL), and chocolate mint flavor (0.5 mL) were added sequentially with stirring. The resulting solution was brought to a final volume of 100 mL by addition of propylene glycol. The final solution was stored at 2°–8° C. until it was filled into 15 mL vials.

The remaining examples provide the preparation of compound III.

EXAMPLE 20

(2S,3S,5S)-5-(N-(N-((N-Methyl-N-((2-isopropyl-4 -thiazolyl)methyl)amino)carbonyl)valinyl)amino)-2-(N-((5-thiazolyl)methoxycarbonyl)amino)-1,6-diphenyl-3-hydroxyhexane.

A. N-(((Benzyl)oxy)carbonyl)-L-phenylalaninal.

A solution of 24.5 ml of anhydrous dimethyl sulfoxide in 870 ml of anhydrous dichloromethane was cooled under $N_2$ atmosphere to −60° C. and treated over a period of 15 min with 131 ml of a 2M solution of oxalyl chloride in dichloromethane in order that the internal temperature remained below −50° C. After addition, the solution was stirred at −60° C. for 15 min and treated over a period of 20 min with a solution of 50 g (0.175 mol) of N-(((benzyl)oxy)-carbonyl-L-phenylalaninol in 200 ml of dichloromethane. The resulting solution was stirred at −60° C. for 1 h, then treated over a period of 15 min with 97 ml of triethylamine in order that the internal temperature remained below −50° C. After addition the solution was stirred at −60° C. for 15 min, then, with the cooling bath in place, was treated rapidly (over a period of 1 min) with a solution of 163 g of citric acid in 550 ml of water. The resulting slurry was stirred vigorously for 10 min, allowed to warm, diluted to 1 liter with water, and separated. The organic layer was washed with 700 ml of water followed by a mixture of 550 ml of water and 150 ml of saturated aqueous $NaHCO_3$, dried over $MgSO_4$, and concentrated in vacuo at 20° C. to give the crude desired compound as a light yellow solid.

B. (2S,3R,4R,5S)-2,5-Bis-(N-(((benzyl)oxy)carbonyl)amino)-3,4-dihydroxy- 1,6-diphenylhexane and (2S,3S, 4S,5S)-2,5-Bis-(N-(((benzyl)oxy)carbonyl)amino)-3,4-dihydroxy-1,6-diphenylhexane.

A suspension of 78.5 g of $VCl_3\cdot(tetrahydrofuran)_3$ and 16 g of zinc dust in 400 ml of dry dichloromethane was stirred under $N_2$ atmosphere for 1 h at 25° C. A solution of 0.175 mol of N-(((benzyl)oxy)carbonyl)-L-phenylalaninal in 200 ml of dichloromethane was then added in one portion, and the resulting mixture was stirred at ambient temperature under $N_2$ atmosphere for 16 h. The resulting mixture was added to 500 ml of 1M aqueous HCl, diluted with 500 ml of hot chloroform, and shaken vigorously for 2 min. The layers were separated, and the organic layer was washed with 1M aqueous HCl and separated. Filtration of the organic phase provided the crude desired product as a solid residue. The residue was slurried in 1.25 liters of acetone, treated with 5 ml of concentrated $H_2SO_4$, and stirred for 16 h at ambient temperature. The resulting mixture was filtered, and the residue (residue A) was washed with 50 ml of acetone. The combined filtrate was concentrated to a volume of 250 ml, diluted with 1000 ml of dichloromethane, washed three times with water and once with saturated brine, dried over $MgSO_4$, and concentrated to give a viscous oil. The oil was taken up in 1000 ml of 1M HCl in methanol (prepared from 71 ml of acetyl chloride and 1000 ml of methanol) and stirred at ambient temperature for 2 h. The resulting precipitate was filtered, washed with methanol, and air-dried on the filter to provide 26.7 g of the desired compound as a white solid. The filtrate was concentrated and filtered to give a second crop (8.3 g) of (2S,3R,4R,5S)-2,5-bis-(N-(((benzyl)oxy)carbonyl)amino)-3,4-dihydroxy-1,6-diphenylhexane. $^1$H NMR ($d_6$-DMSO) δ2.59 (dd, J=13, 5 Hz, 2H), 2.74 (dd, J=13, 9 Hz, 2H), 3.26 (br, 2H), 4.19 (m, 2H), 4.54 (m, 2H), 4.92 (m, 4H), 6.82 (d, J=9 Hz, 2H), 7.0–7.35 (m, 20H). Mass spectrum: $(M+H)^+=569$.

Residue A (above, 2.65 g) was suspended in 75 ml of tetrahydrofuran (THF) and 75 ml of 1M aqueous HCl and heated at reflux for 24 h. After concentration of the resulting solution in vacuo, the residue was taken up in 10% methanol in chloroform, washed two times with water, dried over $Na_2SO_4$, and concentrated in vacuo to provide (2S,3S,4S, 5S)-2,5-bis-(N-(((benzyl)oxy)carbonyl)amino)-3,4-dihydroxy-1,6-diphenylhexane as a white solid. $^1$H NMR ($d_6$-DMSO) δ2.64 (m, 2H), 3.04 (m, 2H), 3.49 (m, 2H), 3.78 (m, 2H), 4.70 (d, J=7 Hz, 2H), 4.93 (AA', 4H), 7.1–7.4 (m, 20H). Mass spectrum: $(M+H)^+=569$.

C. (2S,3R,4S,5S)-3-Acetoxy-2,5-bis-(N-(((benzyl)oxy)carbonyl)amino)-3-bromo-1,6-diphenylhexane.

A suspension of 25 g (44 mmol) of (2S,3R,4R,5S)-2,5-bis-(N-(((benzyl)oxy)carbonyl)amino)-3,4-dihydroxy-1,6-diphenylhexane in 500 ml of 2:1 dichloromethane/hexane was treated with 23 g of α-acetoxyisobutyryl bromide. The resulting mixture was stirred at ambient temperature until the reaction clarified, washed with two 200 ml portions of saturated aqueous $NaHCO_3$, dried over $MgSO_4$, and concentrated in vacuo to give 30.8 g of the crude desired compound. A portion was purified by silica gel chromatography using 9:1 dichloromethane:ethyl acetate to provide the pure desired compound as a white solid. $^1$H NMR ($CDCl_3$) δ2.21 (s, 3H), 2.62 (dd, J=13, 11 Hz, 1H), 2.75 (d, J=7 Hz, 2H), 2.95 (br d, J=15 Hz, 1H), 4.03 (br t, J=10 Hz, 1 h), 4.40 (br d, J=10 Hz, 1H), 4.6–5.0 (m, 6H), 5.12 (br d, J=13 Hz, 1H), 5.33 (br d, J=11 Hz, 1H), 7.0–7.4 (m, 10H). Mass spectrum: $(M+NH_4)^+=690, 692$.

D. (2S,3R,4R,5S)-2,5-Bis-(N-(((benzyl)oxy)carbonyl)amino)-3,4-epoxy-1,6 -diphenylhexane.

A solution of 35.56 g (52.8 mmol) of (2S,3R,4S,5S)-3-acetoxy-2,5-bis-(N-(((benzyl)oxy)carbonyl)amino-3-bromo-1,6-diphenylhexane in 375 ml of dioxane was treated with 255 ml of 1N aqueous sodium hydroxide and stirred at ambient temperature for 16 h, during which the desired compound precipitated. The resulting mixture was filtered, and the residue was washed with water and dried to provide 22.23 g (76%) of the desired compound as a white solid. $^1$H NMR ($CDCl_3$) δ2.7–2.9 (m, 6H), 3.9–4.0 (m, 2H), 4.6–4.7 (m, 2H), 5.03 (m, 4H), 7.1–7.4 (m, 10H).

E. (2S,3S,5S)-2,5-Bis-(N-(((benzyl)oxy)carbonyl)amino)-1, 6-diphenyl-3-hydroxyhexane.

A mixture of 39.2 g (71.2 mmol) of (2S,3R,4R,5S)-2,5-bis-(N-(((benzyl)oxy)carbonyl)amino)-3,4-epoxy-1,6- diphenylhexane in 600 ml of THF was treated under $N_2$ atmosphere with 13 g (0.36 mol) of sodium borohydride. The resulting mixture was treated dropwise with 27.7 ml (0.36 mol) of trifluoroacetic acid. After being stirred for 3.5 h at ambient temperature, the resulting mixture was quenched with 1N aqueous HCl, diluted with water, and stirred for 16 h. The resulting mixture was filtered washed with water, and dried to provide 22.85 g (58%) of the desired compound as a white solid.

F. (2S,3S,5S)-2,5-Diamino-1,6-diphenyl-3-hydroxyhexane.

A suspension of 32 g of the crude resultant compound of Example 20E and 55.5 g (176 mmol) of barium hydroxide octahydrate in 400 ml of 1,4-dioxane and 400 ml of water was heated at reflux for 4 h. The resulting mixture was filtered, and the residue was rinsed with dioxane. The combined filtrates were concentrated to a volume of approximately 200 ml and extracted with four 400 ml portions of chloroform. The combined organic layers were dried over $Na_2SO_4$, filtered, and concentrated in vacuo. The residue was purified by silica gel chromatography using first 2% isopropylamine in chloroform and then 2% isopropylamine/2% methanol in chloroform to provide 10.1 g (81%) of the pure desired compound as a white solid. $^1$H NMR ($CDCl_3$) $\delta$1.54 (dt, J=14, 10 Hz, 1H), 1.67 (dt, J=14, 3 Hz, 1H), 2.50 (dd, J=13, 8 Hz, 1H), 2.58 (dd, J=13,8 Hz, 1H), 2.8 (m, 2H), 2.91 (dd, J=13, 5 Hz, 1H), 3.10 (m, 1H), 3.72 (ddd, J=11,3,2 Hz, 1H), 7.1–7.4 (m, 10H). Mass spectrum: $(M+H)^+$=285.

G. (4S ,6S, 1'S)-6-(1-Amino-2-phenylethyl)-4-benzyl-2-phenyl-3-aza-2bora-1-oxacyclohexane.

A solution of 11.28 g (40 mmol) of (2S,3S,5S)-2,5-diamino-1,6-diphenyl-3-hydroxyhexane and 4.88 g (40 mmol) of phenylboric acid in 1 liter of toluene was heated at reflux and the water azeotropically removed with the aid of a Dean Stark trap until the distillate was clear. The solvent was then removed in vacuo to provide the crude desired compound which was used immediately without further purification.

H. Thioformamide.

To a cooled (0° C.) 2 L three neck round bottom flask equipped with an overhead stirrer charged with a solution of formamide (30.5 mL, 0.76 mol) in 1 L of diethyl ether was added 89 g (0.19 mol) of phosphorous pentasulfide in small portions. The reaction mixture was allowed to warm to ambient temperature, stirred for 2 h, filtered, and concentrated in vacuo to afford thioformamide as a yellow offensive smelling oil which was used without purification.

I. Ethyl 2-Chloro-2-formylacetate.

To a three neck 2 L round bottom flask charged with potassium t-butoxide (0.5 mol, 500 mL of a 1M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over $NaSO_4$, and concentrated in vacuo. The crude desired compound was stored at −30° C. and used without further purification.

J. Ethyl Thiazole-5-carboxylate.

To a round bottom flask was added 250 mL of dry acetone, 7.5 g (0.123 mol) of thioformamide, and 18.54 g (0.123 mol) of ethyl 2-chloro-2 -formylacetate. The reaction was heated at reflux for 2 hours. The solvent was removed in vacuo, and the residue was purified by chromatography ($SiO_2$, 6 cm o.d. column, 100% $CHCl_3$, Rf=0.25) to provide 11.6 g (60%) of the desired compound as a light yellow oil. NMR ($CDCl_3$) $\delta$1.39 (t, J=7 Hz, 3H), 4.38 (q, J=7 Hz, 2H), 8.50 (s, 1H), 8.95 (s, 1H).

K. 5-(Hydroxymethyl)thiazole.

To a precooled (ice bath) three neck 500 mL flask containing lithium aluminum hydride (76 mmol) in 250 mL of THF was added ethyl thiazole-5-carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the filtrate set aside. The crude salts were heated at reflux in 100 mL of ethyl acetate for 30 min. The resulting mixture was filtered, and the two filtrates were combined, dried over $Na_2SO_4$, and concentrated in vacuo. The product was purified by silica gel chromatography eluting sequentially with 0%–2%–4% methanol in chloroform, to provide the desired compound, Rf=0.3 (4% methanol in chloroform), which solidified upon standing in 75% yield. NMR ($CDCl_3$) $\delta$4.92 (s, 2H), 7.78 (s, 1H), 8.77 (s, 1H). Mass spectrum: $(M+H)^+$=116.

L. ((5-Thiazolyl)methyl)-(4-nitrophenyl)carbonate.

A solution of 3.11 g (27 mmol) of 5-(hydroxymethyl)thiazole and excess N-methyl morpholine in 100 ml of methylene chloride was cooled to 0° C. and treated with 8.2 g (41 mmol) of 4-nitrophenyl chloroformate. After being stirred for 1 h, the reaction mixture was diluted with $CHCl_3$, washed successively with 1N HCl, saturated aqueous $NaHCO_3$, and saturated brine, dried over $NaSO_4$, and concentrated in vacuo. The residue was purified by silica gel chromatography (SiO2, 1–2% MeOH/$CHCl_3$, Rf=0.5 in 4% MeOH/$CHCl_3$) to yield 5.9 g (78%) of the desired compound as a yellow solid. NMR ($CDCl_3$) $\delta$5.53 (s, 2H), 7.39 (dt, J=9, 3 Hz, 2H), 8.01 (s, 1H), 8.29 (dt, J=9, 3 Hz, 2 H), 8.90 (s, 1H). Mass spectrum: $(M+H)^+$=281.

M. (2S,3S,5S)-5-Amino-2-(N-((5-thiazolyl)methoxycarbonyl)amino)-1,6-diphenyl-3-hydroxyhexane and (2S,3S,5S)-2-Amino-5-(N-((5-thiazolyl)methoxycarbonyl)amino-1,6-diphenyl-3-hydroxyhexane.

A solution of 500 mg (1.76 mmol) of (2S,3S,5S)-2,5-diamino-1,6-diphenyl-3-hydroxyhexane and 480 mg (1.71 mmol) of ((5-thiazolyl)methyl)-(4-nitrophenyl)carbonate in 20 ml of THF was stirred at ambient temperature for 4 h. After removal of the solvent in vacuo, the residue was purified by silica gel chromatography using first 2% then 5% methanol in chloroform to provide a mixture of the two desired compounds. Silica gel chromatography of the mixture using a gradient of 0–1–2% methanol in 93:2 isopropylamine: chloroform provided 110 mg (16%) of (2S,3S, 5S)-5-amino-2-(N-((5-thiazolyl)-methoxycarbonyl)amino)-1,6-diphenyl-3-hydroxyhexane ($R_f$ 0.48, 96:2:2 chloroform:methanol:isopropylamine) and 185 mg (28%) of (2S,3S,5S)-2-amino-5-(N-((5-thiazolyl)methoxycarbonyl)amino)-1,6-diphenyl-3-hydroxyhexane ($R_f$ 0.44, 96:2:2 chloroform:methanol:isopropylamine).

(2S,3S ,5S )-5-Amino-2-(N-((5-thiazolyl)methoxycarbonyl)amino)-1,6-diphenyl-3-hydroxyhexane: NMR ($CDCl_3$) $\delta$1.3–1.6 (m, 2H), 2.40 (dd, J=14, 8 Hz, 1H), 2.78 (dd, J=5 Hz, 1H), 2.88 (d, J=7 Hz, 2H), 3.01 (m, 1H), 3.72 (br q, 1H), 3.81 (br d, J=10 Hz, 1H), 5.28 (s, 2H), 5.34 (br d, J=9 Hz, 1H), 7.07 (b d, J= 7 Hz, 2H), 7.15–7.35 (m, 8H), 7.87 (s, 1H), 8.80 (s, 1H). Mass spectrum: $(M+H)^+$=426.

(2S,3S,5S)-2-Amino-5-(N-((5-thiazolyl)methoxycarbonyl)amino)-1,6-diphenyl-3-hydroxyhexane: NMR ($CDCl_3$)

δ1.55 (dt, J=14, 8 Hz, 1H), 1.74 (m, 1H), 2.44 (dd, J=15, 1 Hz, 1H), 2.75–3.0 (m, 4H), 3.44 (m, 1H), 4.00 (br t, 1H), 5.28 (m, 3H), 7.1–7.4 (m, 10H), 7.86 (s, 1H), 8.80 (s, 1H). Mass spectrum: (M+H)$^+$=426.

N. (2S,3S,5S)-5-Amino-2-(N-((5-thiazolyl)methoxycarbonyl)amino)-1,6-diphenyl-3-hydroxyhexane.

A solution of 40 mmol of crude (4S,6S,1'S)-6-(1-amino-2-phenylethyl)-4-benzyl-2-phenyl-3-aza-2-bora-1-oxacyclohexane in 700 ml of anhydrous THF was cooled to –40° C. and treated dropwise over a period of 1 h with a solution of 7.83 g (27.9 mmol) of ((5-thiazolyl)methyl)-(4-nitrophenyl)carbonate in 300 ml of dry THF. The resulting solution was allowed to warm to 0° C. for 3 h, then to ambient temperature for 16 h. The solvent was removed in vacuo, and the residue was taken up in 700 ml of ethyl acetate, washed with three 150 ml portions of 1N aqueous NaOH and one 150 ml portion of brine. The organic phase was dried over Na$_2$SO$_4$ and concentrated in vacuo. Purification of the residue by silica gel chromatography using methanol/chloroform mixtures provided the desired compound mixed with its regioisomer. A second chromatography using 1–3% isopropylamine in chloroform provided 5.21 g of the desired compound which solidified upon standing.

O. 2-Methylpropane-thioamide.

A suspension of 100 g (1.15 mol) of isobutyramide in 4 L of diethyl ether was stirred vigorously and treated in portions with 51 g (0.115 mol) of P$_4$S$_{10}$. The resulting mixture was stirred at ambient temperature for 2 h, filtered, and concentrated in vacuo to provide 94.2 g (80%) of the crude desired compound. $^1$H NMR (DMSO-d$_6$) δ1.08 (d, J=7 Hz, 6H), 2.78 (heptet, J=7 Hz, 1H), 9.06 (br, 1H), 9.30 (br, 1H). Mass spectrum: (M+H)$^+$=104.

P. 4-(Chloromethyl)-2-isopropylthiazole hydrochloride.

A mixture of 94.0 g (0.91 mol) of 2-methylpropanethioamide, 115.7 g (0.91 mol) of 1,3-dichloroacetone, and 109.7 g (0.91 mol) of MgSO$_4$ in 1.6 liters of acetone was heated at reflux for 3.5 h. The resulting mixture was allowed to cool, filtered, and the solvent was removed in vacuo to provide the crude desired compound as a yellow oil. $^1$H NMR (DMSO-d$_6$) δ1.32 (d, J=7 Hz, 6H), 3.27 (heptet, J=7 Hz, 1H), 4.78 (s, 2H), 7.61 (s, 1H). Mass spectrum: (M+H)$^+$=176.

Q. 2-Isopropyl-4-(((N-methyl)amino)methyl)thiazole.

A solution of 40 g of 4-(chloromethyl)-2-isopropylthiazole hydrochloride in 100 ml of water was added dropwise with stirring to 400 ml of 40% aqueous methylamine. The resulting solution was stirred for 1 h, then concentrated in vacuo. The residue was taken up in chloroform, dried over Na$_2$SO$_4$, and concentrated in vacuo. Purification of the residue by silica gel chromatography using 10% methanol in chloroform provided 21.35 g (55%) of the desired compound. $^1$H NMR (DMSO-d$_6$) δ1.34 (d, J=7 Hz, 6H), 2.56 (s, 3H), 3.30 (heptet, J=7 Hz, 1H), 4.16 (s, 2H), 7.63 (s, 1H). Mass spectrum: (M+H)$^+$=171.

R. N-(((4-Nitrophenyl)oxy)carbonyl)-L-valine Methyl Ester.

A solution of 66.1 g (0.328 mol) of 4-nitrophenyl chloroformate in 1.2 liters of CH$_2$Cl$_2$ was cooled to 0° C. and treated with L-valine methyl ester hydrochloride. The resulting mixture was treated slowly, with stirring, with 68.9 ml (0.626 mol) of 4-methylmorpholine. The resulting solution was allowed to slowly warm to ambient temperature and was stirred overnight. After washing with 3 portions of 10% aqueous NaHCO$_3$, the solution was dried over Na$_2$SO$_4$ and concentrated in vacuo. The residue was purified by silica gel chromatography by eluting with chloroform to provide the desired compound. $^1$H NMR (DMSO-d$_6$) δ0.94 (d, J=7 Hz, 3H), 0.95 (d, J=7 Hz, 3H), 2.12 (octet, J=7 Hz, 1H), 3.69 (s, 3H), 4.01 (dd, J=8, 6 Hz, 1H), 7.41 (dt, J=9, 3 Hz, 2H), 8.27 (dt, J=9, 3 Hz, 2H), 8.53 (d, J=8 Hz, 1H). Mass spectrum: (M+NH$_4$)$^+$=314.

S. N-((N-Methyl-N-((2-isopropyl-4-thiazolyl)methyl)amino)carbonyl)-L-valine Methyl Ester.

A solution of 15.7 g (92 mmol) of 2-isopropyl-4-(((N-methyl)amino)-methyl)thiazole in 200 ml of THF was combined with a solution of 20.5 g (69 mmol) of N-(((4-nitrophenyl)oxy)carbonyl)-L-valine methyl ester. The resulting solution was treated with 1.6 g of 4-dimethylaminopyridine and 12.9 ml (92 mmol) of triethylamine, heated at reflux for 2 h, allowed to cool, and concentrated in vacuo. The residue was taken up in CH$_2$Cl$_2$, washed extensively with 5% aqueous K$_2$CO$_3$, dried over Na$_2$SO$_4$, and concentrated in vacuo. The resulting product mixture was purified by silica gel chromatography using chloroform as an eluent to provide 16.3 g (54%) of the desired compound. $^1$H NMR (DMSO-d$_6$) δ0.88 (d, J=7 Hz, 3H), 0.92 (d, J=7 Hz, 3H), 1.32 (d, J=7 Hz, 3H), 2.05 (octet, J=7 Hz, 1H), 2.86 (s, 3H), 3.25 heptet, J=7 Hz, 1H), 3.61 (s, 3H), 3.96 (dd, J=8, 7 Hz, 1H), 4.44 (AA', 2H), 6.58 d, J=8 Hz, 1H), 7.24 (s, 1H). Mass spectrum: (M+H)$^+$=328.

T. N-((N-Methyl-N-((2-isopropyl-4-thiazolyl)methyl)amino)carbonyl)-L-valine.

A solution of 1.42 g (4.3 mmol) of the resultant compound of Example 20S in 17 ml of dioxane was treated with 17.3 ml of 0.50M aqueous LiOH. The resulting solution was stirred at ambient temperature for 30 min, treated with 8.7 ml of 1M HCl, and concentrated in vacuo. The residue was taken up in dichloromethane, washed with water, dried over Na$_2$SO$_4$, and concentrated in vacuo to provide 1.1 g (81%) of the desired compound. Mass spectrum: (M+H)$^+$=314.

U. (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane.

A solution of 70 mg (0.223 mmol) of N-((N-methyl-N-((2-isopropyl-4-thiazolyl)methyl)amino)carbonyl)-L-valine, 79 mg (0.186 mmol) of (2S,3S,5S)-5-amino-2-(N-((5-thiazolyl)methoxycarbonyl)amino)-1,6-diphenyl-3-hydroxyhexane, 30 mg (0.223 mmol) of 1-hydroxybenzotriazole hydrate, and 51 mg (0.266 mmol) of N-ethyl-N'-dimethylaminopropyl carbodiimide in 2 ml of THF was stirred at ambient temperature for 16 h. The resulting solution was concentrated in vacuo, and the residue was purified by silica gel chromatography using 97:3 CH$_2$Cl$_2$:CH$_3$OH to provide 100 mg (74%) of the desired compound (R$_f$0.4, 95:5 CH$_2$Cl$_2$:CH$_3$OH) as a solid, mp 61°–63° C. Mass spectrum: (M+H)$^+$=721. Anal. Calcd for C$_{37}$H$_{49}$N$_6$O$_5$S$_2$.0.5H$_2$O: C, 60.88; H, 6.77; N, 11.51. Found: C, 60.68; H, 6.53; N, 11.36.

EXAMPLE 21

(2S,3S,5S)-2-Amino-3-hydroxy-5-(t-butyloxycarbonylamino)-1,6-diphenylhexane.

EXAMPLE 21A (2S,3 S,5S)-2-(N,N-dibenzylamino)-3-hydroxy-5-(t-butyloxycarbonylamino)-1,6-diphenylhexane.

To a stirred solution of (2S,3S,5S)-2-(N,N-dibenzylamino)-3-hydroxy-5-amino-1,6-diphenylhexane (10.0 g, 21.6 mmol) in tetrahydrofuran (200 mL) was added potassium carbonate (6.0 g, 43.2 mmol) in H$_2$O (200 mL). To this solution was added di-t-butyldicarbonate (5.64 g, 25.9 mmol) in tetrahydrofuran (10 mL). The solution which resulted was stirred at room temperature for 3 hours. N,N-dimethylethylenediamine (1 mL, 8.6 mmol) was added and the reaction mixture was stirred at room temperature for an additional hour. Ethyl acetate (400 mL) was added and the organic layer was separated and washed with 5% KH$_2$PO$_4$ (2×200 mL), water (1×200 mL), saturated NaHCO$_3$ (2×200 mL) and water (1×200 mL). The organic solution was then dried over sodium sulfate and concentrated under reduced pressure to provide the desired product as a light yellow oil. 300 MHz $^1$H NMR (CDCl$_3$) δ1.40 (s,9H), 1.58 (s, 2H), 2.45–2.85 (m, 4H), 3.05 (m, 1H), 3.38 (d, 2H), 3.6 (m, 1H), 3.79 (m, 1H), 3.87 (d, 2H), 4.35 (s, 1H), 4.85 (s, broad, 1H), 7.0–7.38 (m, 20H).

EXAMPLE 21B (2S,3S,5S)-2-amino-3-hydroxy-5-(t-butyloxycarbonylamino)-1,6-diphenylhexane.

To a stirred solution of (2S,3S,5S)-2-(N,N-dibenzylamino)-3-hydroxy-5-(t-butyloxycarbonylamino)-1,6-diphenylhexane (12 g, 21.3 mmol) in methanol (350 mL) was charged ammonium formate (8.05 g, 128 mmol, 6.0 eq) and 10% palladium on carbon (2.4 g). The solution was stirred under nitrogen at 60° C. for three hours and then at 75° C. for 12 hours. An additional amount of ammonium formate (6 g) and 10% palladium on carbon (1.5 g) was added as well as 1 mL of glacial acetic acid. The reaction was driven to completion within 2 hours at a reflux temperature. The reaction mixture was then cooled to room temperature and then filtered through a bed of celite. The filter cake was washed with methanol (75 mL) and the combined filtrates were concentrated under reduced pressure. The residue was taken up in 1N NaOH (300 mL) and extracted into methylene chloride (2×200 mL). The combined organic layers were washed with brine (250 mL) and dried over sodium sulfate. Concentration of the solution under reduced pressure provided the desired product as a light colored oil which slowly crystallized upon standing (5 g). Further purification of the product could be accomplished by flash chromatography (silica gel, 5% methanol in methylene chloride). 300 MHz$^1$H NMR (CDCl$_3$) δ1.42 (s, 9H), 1.58 (m, 1H), 1.70 (m, 1H), 2.20 (s, broad, 2H), 2.52 (m, 1H), 2.76–2.95 (m, 4H), 3.50 (m, 1H), 3.95 (m, 1H), 4.80 (d, broad, 1H), 7.15–7.30 (m, 10H).

EXAMPLE 22

Alternative Preparation of (2S,3S,5S)-2-Amino-3-hydroxy-5-(t-butyloxycarbonylamino)-1,6-diphenylhexane.

EXAMPLE 22A (5S)-2-(t-Butyloxycarbonylamino)-5-(N,N-dibenzylamino)-1,6-diphenyl-4-oxo-2-hexene To 9.21 gm (20 mmol) of (S)-2-amino-5-(N,N-dibenzylamino)-1,6-diphenyl-4-oxo-2-hexene and 0.37 gm (3 mmol) 4-N,N-dimethylaminopyridine in 100 ml of methyl tert-butylether was added via syringe pump a solution containing 4.80 gm (22 mmol) di-tert-butyl dicarbonate in the same solvent (25 ml) over a period of 6 h. An additional amount (3 ml) of methyl tert-butylether was then added to complete the addition. After stirring at room temperature for 18 h the reaction mixture was cooled with the aid of an ice water bath. The resultant solid was collected by suction filtration and washed with cold (0° C.) methyl tert-butylether and hexane and dried under vacuum to give 9.9 gm of crude material as a white solid. The material thus isolated was dissolved in a minimal amount of dichloromethane and purified by flash chromatography on silica gel. Elution of the column with a mixture of hexane-ethyl acetate-dichloromethane (8:1:1) gave, after concentration of the appropriate fractions, 8.1 gm (72%) of the desired compound. Mp. 191°–193° C. [α]$_D$ −183.7° (c=1.05, CHCl$_3$). $^1$H NMR (CDCl$_3$, δ): 11.68 (bs, 1H), 7.05–7.47 (m, 20H), 5.28 (s,1H), 4.27 (d, J=16 Hz, 1H), 4.02 (d, J=16 Hz, 1H), 3.58 (m, 4H), 3.40 (m, 1H), 3.11 (m, 1H), 2.90 (m, 1H), 1.48 (s, 9H).

EXAMPLE 22B

Alternate preparation of (5S)-2-(t-Butyloxycarbonylamino)-5-(N,N-dibenzylamino)-1,6-diphenyl-4-oxo-2-hexene A suspension of (S)-2-amino-5-(N,N-dibenzylamino)-1,6-diphenyl-4-oxo-2-hexene (100.0 g, 0.217 mol) in 15% ethyl acetate/hexanes (2 liters) under N$_2$ was warmed to about 40° C. The resulting solution was cooled to room temperature before adding 4.0 g (33 mmol) of N,N-dimethyl-4-aminopyridine and 49.7 g (0.228 mol) of di-tert-butyl dicarbonate. The reaction mixture was allowed to stir overnight at room temperature. (After approximately one hour, a white precipitate began to form.) The suspension was filtered and the precipitate was washed with hexanes to afford the desired product as colorless crystals. TLC: 25% ethyl acetate/hexanes R$_f$ 0.38.

EXAMPLE 22C (2S,3S,5S)-2-(N,N-Dibenzylamino)-5-(t-butyloxycarbonylamino)-3-hydroxy-1,6-diphenylhexane.

A solution of the product of Example 22A (5 g, 8.9 mmol) in dichloromethane (100 ml) and 1,4-dioxolane (100 ml) was cooled to between −10° and −15° C. and treated dropwise with 1M BH$_3$THF (26.7 ml, 26.7 mmol). The solution was stirred at this temperature for 3 hr. The clear solution was quenched with excess methanol (20 ml) and stirred at room temperature for 30 min. The solvent was removed in vacuo.

The resulting white foam was dissolved in THF (75 ml) and cooled to −40° C. A solution of LAH (9 ml, 1M in THF, 9 mmol) was added dropwise. After 10 min. the solution was quenched with water followed by dilute aqueous HCl. The organics were removed and the aqueous layer extracted with ethyl acetate (3×20 ml). The combined organics were washed (saturated aqueous bicarbonate followed by brine), dried (Na$_2$SO$_4$), filtered and evaporated to afford 4.9 g (99%) of the desired product as a white foam.

Alternatively, the white foam resulting from the BH$_3$THF reaction step was dissolved in MeOH (45 ml), cooled to +3° C. and treated portionwise with KBH$_4$ (1.44 g, 26.7 mmol). After addition of the last portion of KBH$_4$ the reaction was stirred for an additional 4 hours at +4° to +5° C. The solution was concentrated by ½ the volume/n vacuo, diluted with 1/1 hexane-EtOAc (70 ml) and quenched (with cooling, maintain temp. <30 ° C.) by adding a 10% solution of KHSO$_4$ to pH=about 5. NaOH (15% aqueous) was added to pH=12–13. The insoluble salts were removed by filtration, and the filter cake washed 3 times with 7 ml 1/1 hexane/EtOAc. The filtrate and washes were transferred to a separatory funnel, diluted with 15 ml hexane and 15 ml H₂O. The organics were removed and the aqueous layer was extracted once with 20 ml (1/1) hexane-EtOAc. The combined organics were washed (saturated brine), dried ($Na_2SO_4$), filtered, and evaporated to afford 5.2 g of the desired product which was used without further purification in subsequent reactions.

$R_f$ 0.5 (25% EtOAc/hexane) $^1$H NMR ($CDCl_3$) δ7.37–7.10 (m 20H); 6.78 (br. s, 1H); 4.62 (d, 1H); 4.50 (s, 1H); 4:18 (dd, 1H); 3.9 (d, 2H); 3.65 (dd, 2H); 3.40 (d, 2H); 3.00 (m, 2H); 2.77 (m, 1H); 1.39 (s, 9H). MS (EI) m/e565 (M+H).

EXAMPLE 22D (2S,3S,5S)-2-Amino-3-hydroxy-5-(t-butyloxycarbonylamino)-1.6-diphenylhexane.

A solution of the product from Example 22C (150 gm, 250 mmol) dissolved in absolute EtOH (2 liters) was treated with 10% Pd/C (18 gm, pre-wetted), followed by addition of ammonium formate (78.6 gms, 1.25 moles) dissolved in H₂O (200 ml). The resulting mixture was stirred at reflux for 2.5 hours. The mixture was cooled to room temperature and filtered through a pad of infusorial earth (20 g). The filter cake was washed 3 times with EtCH (70 ml each). The filtrate was concentrated in vacuo. The residue was dissolved into EtOAc (1 L) and washed (1N NaOH, followed by H₂O, followed by brine), dried ($Na_2SO_4$), filtered and concentrated in vacuo. to a constant weight of 95 gms. (99.2% of theory). The light yellow solid (91.5 gm of the 95 gm) was slurried in hot heptane (600 ml) (steam bath) and treated with isopropanol (45 ml), and swirled to effect solution. The solution was allowed to slowly cool to room temperature over 3 hours, kept at room temperature for 2 more hours and filtered. The filter cake was washed 10 times with 9/1 hexane-isopropanol (30ml each) to give the desired product as an off-white finely crystalline solid which was dried to constant weight of 57.5 gm.

The crude product (20 gm) was recrystallized from hot 140 ml heptane/17 ml isopropanol. After letting the solution cool slowly to room temperature, the mixture was let stand at room temperature for 2 hours and then filtered. The filter cake was rinsed (5×15 ml (8/1) heptane/isopropanol) and dried to a constant weight of 18.5 gm.

EXAMPLE 23

Alternative Preparation of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1.6-diphenyl-3-hydroxyhexane

EXAMPLE 23A (2S,3S,5S)-5-(t-Butyloxycarbonylamino)-2-(N-((5-thiazolyl)methoxycarbonyl)amino)-1.6-diphenyl-3-hydroxyhexane The product of Example 22D (6.0 g , 15.6 mmoles) was dissolved in 60 mL of DMF under nitrogen atmosphere. To this stirred solution at room temperature was added 5-(p-nitrophenyloxycarbonyloxymethyl)thiazole (4.67 g, 15.6 mmole) and the resulting solution was stirred for 4 h. The solvent was removed under reduced pressure by rotary evaporation and the residue dissolved in 150 mL EtOAc. This solution was washed with 5×75 mL 1N NaOH solution, 100 mL brine, dried over $Na_2SO_4$. The solvent was removed to afford 8.02 g of a slightly yellowish oil. This material was crystallized from 30 mL EtOAc and 40 mL hexane to afford 6.53 g (80%) of the desired product as a white solid. mp 118°–120° C. H $^1$NMR ($CDCl_3$) δ8.79 (s, 1H), 7.83 (s, 1H), 7.30–7.15 (m, 8H), 7.08 (m, 2H), 5.23 (s, 2H), 5.14 (d, 1H, J=9 Hz), 4.52 (m, 1H), 3.92–3.72 (m, 3H), 3.65 (m, 1H), 2.85 (d-apparent, 2H, J=7.5 Hz), 2.72 (d-apparent, 2H, J=7 Hz), 1.61 (m, 2H), 1.38 (s, 9H). CIMS m/z (526) (M+H)⁺, 543 (M+18)⁺.

EXAMPLE 23B (2S,3S,5S)-5-Amino-2-(N-((5-thiazolyl)methoxycarbonyl)amino)-1,6-diphenyl-3-hydroxyhexane The product of Example 23A (6.43 g, 12.23 mmoles) was dissolved in 25 mL dioxane at room temperature under nitrogen atmosphere. To this stirred solution was added 20.25 mL of 4N HCl in dioxane, and after approximately 10 min a thick precipitate formed. An additional 10 mL of dioxane was added to loosen up the slurry. This mixture was stirred for 1 h and then filtered. The filter cake of the product bis-HCl salt was washed with 20 mL dioxane, air dried, and then dissolved in 175 mL water. To this solution was added 175 mL ethyl acetate and the two phase mixture rapidly stirred. The pH of this mixture was adjusted to pH=10 by the dropwise addition of 3N NaOH to the rapidly stirred mixture. The organic layer was isolated, washed with brine (150 mL), and dried over $Na_2SO_4$. The solvent was removed to afford 5.18 g (99%) of the desired product as a clear oil. H $^1$ NMR ($CDCl_3$) δ8.81 (s, 1H), 7.87 (s, 1H), 7.35–7.05 (m, 10H), 5.33 (d, 1H, J=9.3 Hz), 5.28 (m,2H), 3.81 (m, 1H), 3.72 (m, 1H), 3.01 (m, 1H), 2.88 (m, 2H), 2.78 (dd, 1H, J=13.5, 5.1 Hz), 2.39 (dd, 1H, J=9.0, 4.5 Hz), 1.57–1.30 (m, 2H). CIMS m/z 426 (M+H)⁺.

EXAMPLE 23C (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1.6-diphenyl-3-hydroxyhexane N-((N-Methyl-N-((2-isopropyl-4-thiazolyl)methyl)amino)carbonyl)-L-valine (4.13 g, 13.18 mmole) and hydroxybenztriazole (2.23 g, 16.48 mmoles) were dissolved in 70 mL THF and then dicyclohexyl-carbodiimide(2.71 g, 13.18 mmoles) was added in one portion to the stirred solution under nitrogen atmosphere. This mixture was stirred for 4 h at room temperature and then filtered to remove dicyclohexylurea precipitate. (2S,3S,5S)-5-Amino-2-(N-((5-thiazolyl)-methoxycarbonyl)amino)-1,6-diphenyl-3-hydroxyhexane (5.1 g, 11.99 mmoles) was dissolved in 100 mL THF under nitrogen atmosphere. To this stirred solution was added the filtrate of HOBT-active ester and the resulting solution was stirred at room temperature for 4 h, and the solvent removed via rotary evaporation. The residue was dissolved in 150 mL ethyl acetate and washed with 2×100 mL 1N NaOH, 100 mL brine, 100 mL of 1% w/w aqueous KHSO₄ and the solvent was removed by rotary evaporation to afford a residue. The residue was dissolved in 175 mL 1N HCL, and the solution filtered to remove the small quantity of dicyclohexylurea. The filtrate solution was added to 175 mL ethyl acetate and the two phase mixture rapidly mixed. The pH of this rapidly stirred mixture was adjusted to pH=7 by dropwise addition of cold 3N NaOH. The organic layer was isolated, washed with 100 mL brine, dried over Na$_2$SO$_4$, filtered, and the solvent was removed to afford 8.6 g of a colorless foam. This material was crystallized from 42 mL EtOAc and 21 mL hexane to give 7.85 g of the desired product as a white solid. mp=122°–123° C. CIMS m/z 721 (M+H)$^+$.

EXAMPLE 24

Alternative Preparation of (2S,3S,5S)-5-Amino-2-(N-((5-thiazolyl)methoxycarbonyl)amino)-1.6-diphenyl-3-hydroxyhexane Alternative A The product of Example 17F (9.5 g, 33.4 mmol) and phenylboronic acid (4.1 g, 33.6 mmol) were combined in toluene (150 mL) and refluxed for 2.5 hours with azeotropic water removal (Dean-Stark trap). Toluene (100 mL) was distilled out at atmospheric pressure, then the remaining toluene was removed under vacuum, to provide a yellow syrup which was dissolved in DMF (50 mL) and cooled to –60 ° C. A solution of 5-(p-nitrophenyloxycarbonyloxymethyl)thiazole (9.5 g, 33.5 mmol) in DMF (50 mL) was added over 45 minutes. The resulting mixture was stirred for 8 hours at –55°±5° C., then 14 hours at –25° C., then was allowed to warm to room temperature. The reaction mixture was diluted with 1N HCl (250 mL) and washed with CH$_2$Cl$_2$ (2×80 mL). The combined organic layers were back-extracted with 1N HCl (60 mL). The combined aqueous HCl layers were cooled in an ice-bath to 2° C., and conc. (37%) HCL (30 mL) was added over 5 minutes. The desired product (bis HCl salt) began to precipitate within 30 minutes. The slurry was stirred 3 hours at 2–5° C., then the product (bis HCl salt) was collected by filtration and dried in a vacuum oven at 55°–60 ° C. Yield 11.4 g (68%).

Second crop recovery:

The HCl mother liquors were stirred with ethyl acetate (190 mL) and neutralized to pH 9–10 with aqueous K$_2$CO$_3$ (200–300 g of 25% w/w K$_2$CO$_3$ was required). The ethyl acetate layer was concentrated under vacuum to an oil which was redissolved in 1N HCl (90 mL) and washed with methylene chloride (45 mL). The aqueous layer was cooled to 2° C. Conc. (37%) HCl (9.0 mL) was added to precipitate a second crop. After stirring for 1–3 hours at 2–5° C., the solid was collected by filtration and dried in a vacuum oven at 55°–60 ° C. Yield 2.1 g (12.6%).

Neutralization of Bis HCl Salt:

The bis HCl salt (10.66 g, 21.4 mmol, mixture of first and second crops) was stirred with CH$_2$Cl$_2$ (110 mL) and 5% aqueous NaHCO$_3$ (110 mL) until all solids dissolved (2 hours). The aqueous layer was separated and extracted with another 50 mL CH$_2$Cl$_2$. The combined organic extracts were dried with Na$_2$SO$_4$ (10 g), filtered and concentrated under vacuum at ≦40° C. to an oil. The oil was dried on a vacuum pump to give the title compound as a yellow foam, 9.1 g ( 100 %).

Alternative B

The product of Example 17F (15.0 g, 0.053 mole) was dissolved in DMF (75 mL). Triisopropylborate (24.4 mL, 0.105 mole) was added and stirred at ambient temperature for approximately 1.5 hours. The solution was cooled to –10° C. and a solution of 5-(p-nitrophenyloxycarbonyloxymethyl)thiazole (15.0 g, 0.054 mole) in DMF (75 mL) was added over 80 minutes. The reaction was stirred for approximately 1 hour at –10 ° C., then was diluted with methylene chloride (250 mL) and quenched with a mixture of triethanolamine (24.8 g) and 5% aqueous sodium bicarbonate (300 mL). The biphasic mixture was stirred for 1 hour, then the layers were separated and the aqueous was extracted with another portion of methylene chloride (50 mL). The combined organic layers were extracted with 1N HCl (1×390 mL, then 1×95 mL). The acid layers were combined, cooled in an ice-bath, and further acidified with conc. HCl (50 mL) which produced a white slurry of product. The slurry was stirred for approximately 1 hour at 2° C. The desired product bis HCl salt) was collected by filtration and dried at 55° C. in a vacuum oven. Yield 18.5 g (70%).

EXAMPLE 25

Alternative Preparation of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1.6-diphenyl-3-hydroxyhexane To a solution of the product of Example 24 (9.1 g, 21.4 mmol), HOBT (3.6 g, 23.5 mmol) and N-((N-Methyl-N-((2-isopropyl-4-thiazolyl)methyl)amino)-carbonyl)-L-valine (7.37 g, 23.5 mmol) in THF (170 mL) was added DCC (4.85 g, 23.5 mmol). The solution was stirred at ambient temperature for 16 hours (DCU precipitates). THF was removed under vacuum and the resulting paste was stirred with cold 1N HCl (106 mL at 5° C.) for 3 hours to dissolve the the crude product. The DCU was removed by filtration and the filter cake was washed with 1N HCl (30 mL). KH$_2$PO$_4$ (3.2 g) was dissolved in the combined HCl filtrates. The solution was mixed with ethyl acetate (80 mL) and neutralized to pH 7 with aqueous NaOH (60.3 g of 10% w/w NaOH). The aqueous layer was extracted with another 25 mL ethyl acetate and the combined ethyl acetate extracts were washed with aqueous NaHCO$_3$ (2×37 mL of 5% w/w NaHCO$_3$). The organic layer was dried with Na$_2$SO$_4$ (13 g), filtered, and concentrated under vacuum at <45° C. The residue was dissolved in a 1:1 ethyl acetate/heptane mixture (200 mL) at 70° C. The solution was allowed to cool slowly and stirred overnight at room temperature to provide a thick slurry. The product was collected by filtration and washed with 1:1 ethyl acetate/heptane (20 mL). The product was dried briefly at 55° C. in a vacuum oven to obtain an approximate weight prior to the second crystallization (12.85 g, 83%).

A second crystallization from 144 mL of 2:1 ethyl acetate/heptane (dissolved at 70 ° C, then stirred at room temperature 12 hours) produced a thick slurry of fine white solid. The product was collected by filtration and washed with 15 mL 2:1 ethyl acetate/heptane, then dried in a vacuum oven at 55 ° C. for 2 days to give the desired product. Yield 11.9 g (77%).

EXAMPLE 26

Alternate Preparation of ((5-Thiazolyl)methyl)-(4-nitrophenyl)carbonate

EXAMPLE 26A

2-Amino5-(ethoxycarbonyl)thiazole Hydrochloride

To a –10° C. solution of potassium tert-butoxide (110 g, 0.98 mol) in THF (1.9 L) was added a solution of ethyl chloroacetate (100 mL, 0.934 mol) and ethyl formate (75 mL, 0.928 mol) in THF (400 mL) dropwise over 2 hours, with good mechanical stirring. The thick solution was stirred another 2 hours at ca. −1 °C. then the reaction was quenched by addition of a solution of NaCl (150 g) in 1N HCL (750 mL). The mixture was allowed to warm to 20° C. and the lower aqueous layer (containing some precipitated salt) was separated. The organic layer was stripped under vacuum on a rotary evaporator. The oil was redissolved in 500 mL ethyl acetate, dried with 75 g $Na_2SO_4$ for 1 hour, filtered and concentrated under vacuum (40°–50° C. bath temperature) to an oil. The resulting crude chloroaldehyde (161 g) and thiourea (70 g, 0.92 mol) were dissolved in THF (2 L) and warmed to gentle reflux (60° C.). The thiourea dissolved during warming, and within 20 minutes, product precipitated from solution. After 100 minutes the suspension was allowed to cool to room temperature, then was cooled in an ice-bath for 1 hour. The product was collected on a fitted Buchner funnel and washed with 2×100 mL cold THF, then dried overnight in a vacuum oven at 50° C. Yield: 122 g of title compound as a tan-colored solid, m.p. 182°–185° C. (dec.). $^1$H NMR (DMSO-$d_6$) δ7.86 (s, 1H), 4.19 (q, 2H), 1.21 (t, 3H). $^{13}$C NMR (DMSO-$d_6$) δ171.9, 160.4, 140.4, 114.4, 61.1, 14.2.

EXAMPLE 26B

2-Amino-5-(ethoxycarbonyl)thiazole

To a −10° C. solution of potassium tert-butoxide (150 g, 1.3 mol) in THF (1.35 L) was added a solution of ethyl chloroacetate (139 mL, 1.3 mol) and ethyl formate (103 mL, 1.27 mol) in THF (150 mL) dropwise over 75 minutes, with good mechanical stirring. A THF rinse (25 mL) was added over 5 minutes. The thick solution was stirred another 3 hours at ca. −5° to 0° C., then the reaction was quenched by addition of a solution of NaCl (240 g) and conc. HCl (90 mL) in water (960 mL). The mixture was allowed to warm to 15° C. and the lower aqueous layer was discarded. Thiourea (97 g, 1.27 mol) was dissolved in the crude THF solution of chloroaldehyde. The solution was warmed to 65° C. and refluxed for 1 hour, then cooled to 30° C. Addition of a solution of $K_2CO_3$ (88 g, 0.64 mol) in 1500 mL water produced two layers (aqueous pH=7). The THF was removed under vacuum at ≦45° C., causing the product to precipitate as a yellow solid. The slurry was cooled to 15° C., and the product was collected on a fitted Buchner funnel and washed with 3×200 mL water, then dried 24 hours in a vacuum oven at 55° C. to provide 151 g of title compound as a yellow solid, m.p. 155°–158° C. $^1$H NMR (DMSO-$d_6$) δ7.8 (br s, 2H, $NH_2$), 7.62 (s, 1H), 4.13 (q, 2H), 1.18 (t, 3H). $^{13}$C NMR (DMSO-$d_6$) δ173.4, 161.3, 147.9, 114.5, 60.1, 14.3.

EXAMPLE 26C 5-(Ethoxycarbonyl)thiazole

A solution of 2-amino-5-(ethoxycarbonyl)thiazole (50 g, 0.29 mmol) in a mixture of DMF (83 mL) and THF (317 mL) was added dropwise over 87 minutes to a stirred 41° C. solution of isoamyl nitrite (59 mL, 0.44 mol) in DMF (130 mL). A maximum temperature of 60° C. was observed during the exothermic addition. After another 40 minutes the THF was removed under vacuum at 45° C. The concentrated DMF solution was cooled to 25° C. and diluted with toluene (420 mL) and water (440 mL). The toluene layer was extracted with 3×120 mL water, then dried with $Na_2SO_4$ (50 g) for 1 hour. After filtration the toluene layer was stripped on a rotary evaporate at 50° C. bath temperature, then on a vacuum pump at 21° C. The crude residue containing the title compound weighed 65.6 g. This material was used directly in the next step. A sample of similarly prepared material was purified by column chromatography to give a yellow oil. $^1$H NMR (CDCl$_3$) δ8.95 (s, 1H), 8.51 (s, 1H), 4.39 (q, 2H), 1.40 (t, 3H). $^{13}$C NMR (CDCl$_3$) δ161.0, 157.9, 148.6, 129.8, 61.6, 14.1.

EXAMPLE 26D 5-(Hydroxymethyl)thiazole

To a slurry of lithium aluminum hydride (9.0 g) in THF (633 mL) was added a solution of crude 5-(ethoxycarbonyl)thiazole (65.6 g) in THF (540 mL) over 95 minutes at 0°–5° C. After an additional 25 minutes, tile reaction was quenched at 5° C. by sequential addition of water (8.1 mL), 15% NaOH (8.1 mL), and water (24.3 mL). After drying with $Na_2SO_4$ (44 g) for 2 hours, the slurry was filtered, and the filter cake was washed with 100 mL THF. The combined filtrates were concentrated under vacuum at 45° C. to a brown oil (39 g). The oil was fractionally distilled through a short-path apparatus. The product fractions distilled at 97°–104° C. vapor temperature at 3–5 mm, providing 20.5 g of the title compound as a turbid orange oil. $^1$H NMR (CDCl$_3$) δ8.74 (s, 1H), 7.72 (s, 1H), 4.89 (s, 2H), 3.4 (br s, 1H, OH). $^{13}$C NMR (CDCl$_3$) δ153.4, 140.0, 139.5, 56.6.

EXAMPLE 26E 5-(p-Nitrophenyoxycarbonyloxymethyl)thiazole Hydrochloride

Distilled 5-(hydroxymethyl)thiazole (14.1 g, 123 mmol) and triethylamine (17.9 mL, 129 mmol) were dissolved in ethyl acetate (141 mL) and cooled to −1° C. (ice/salt bath). A solution of 4-nitrophenyl chloroformate (26.0 g, 129 mmol) dissolved in ethyl acetate (106 mL) was added dropwise over 50 minutes at an internal temperature of 0°–4° C. An ethyl acetate flask rinse (20 mL) was also added. Salts precipitated from solution throughout the addition. The yellow mixture was stirred another 1 hour 45 minutes at 0°–2° C., then a solution of dilute HCl (3.1 g, 31 mmol of conc. HCl in 103 mL water) was added at once. The mixture was stirred for 0.5 hours while warming to 15° C., then stirring was stopped. The organic layer was washed twice with aqueous 5% $K_2CO_3$ solution (2×70 mL), then dried with $Na_2SO_4$ (30 g). After filtration the solution was concentrated under vacuum on a rotary evaporate (bath temperature of 41° C.) to a brown oil (38g). The crude 5-(p-nitrophenyoxycarbonyloxymethyl)-thizaole was dissolved in ethyl acetate (282 mL), then cooled in an ice bath to 2° C. Dry HCl gas (7.1 g, 195 mmol) was bubbled in slowly over 50 minutes (temperature 2°–4° C.). After stirring for another 1 hour 45 minutes at 2°–4° C., the solid precipitate was collected on a sintered glass funnel under a nitrogen blanket and the flask was washed out with 50 mL cold ethyl acetate which was used to rinse the filter cake. The cake was dried on the funnel under strong nitrogen purge for 15 minutes then dried in a vacuum oven at 50° C. with a nitrogen purge to provide 29.05 g of the title compound as tan powder, m.p. 131°–135° C. (dec.). $^1$H NMR (DMSO-$d_6$) δ9.21 (d, 1H), 8.27 (m, 2H), 8.06 (d, 1H), 7.52 (m, 2H), 5.54 (s, 2H). $^{13}$C NMR (DMSO-$d_6$) δ157.3, 155.2, 151.8, 145.3, 143.7, 131.9, 125.5, 122.7, 62.1.

EXAMPLE 26F

5-(p-Nitrophenoxycarbonyloxymethyl)thiazole 5-(p-Nitrophenoxycarbonyloxymethyl)thiazole hydrochloride (3.0 g) was slurried in ethyl acetate (30 mL) and cooled to 10°–15° C. A solution of 5% aqueous potassium carbonate (30 mL) was added with rapid stirring. After 15 minutes, stirring was stopped and the aqueous layer was separated. The organic layer was dried with $Na_2SO_4$ (3 g), filtered, and solvent was distilled under vacuum to give 2.49 g of the title compound as a brown syrup which slowly solidified, m.p. 62°–64° C. $^1$H NMR ($CDCl_3$) δ8.90 (d, 1H), 8.29 (m, 2H), 8.01 (d, 1H), 7.39 (m, 2H), 5.52 (s, 2H). $^{13}$C NMR ($CDCl_3$) δ155.4, 155.2, 152.2, 145.4, 144.9, 130.6, 125.3, 121.6, 61.9.

EXAMPLE 27

Alternative Preparation of N-((N-Methyl-N-((2isopropyl-4-thiazolyl)methyl)amino)carbonyl)-L-valine

EXAMPLE 27A

Thioisobutyramide

To a 1 liter three neck round bottom flask equipped with mechanical stirrer, nitrogen atmosphere, condensor, thermocouple and 15° C. water bath was charged (26.0 g, 0.298 mols) isobutyramide followed by (19.9 g, 0.045 mols) phosphorous pentasulfide and 375 mls THF. This solution was stirred at 20°±5° C. for 3 hours, then was warmed to 60° C. and stirred an additional 3 hours. The THF was removed under vacuum with a 50° C. bath temperature to afford a yellow oil. This oil was neutralized with a solution of 5 g NaOH, 10 g NaCl and 90 g water. Next the product was extracted into EtOAc (2×250 mls) and the combined organics reduced under vacuum to an oil. The oil was dissolved in 50 mls THF and again the solvent was removed under vacuum to give the desired product as a yellow oil. (yield approx. 27 grams, 88%).

EXAMPLE 27B

2-Isopropyl-4(((N-methyl)amino)methyl)thiazole

The thioisobutyramide resulting from Example 24A was dissolved in 70 mls THF and added slowly to a solution of (34.1 g, 0.27 mols) 1,3-dichloracetone in 40 mls THF. A 10 ml rinse of THF was used to completely transfer the thioamide. The reaction was carried out in a 250 ml flask with mechanical stirring under nitrogen atmosphere. The reaction temperature was maintained below 25° C. during addition with a 15°±5° C. bath. The bath was kept in place for 1 hour after which it was removed and the reaction stirred for 18 hours. Next this stirred chloromethyl-thiazole solution was added to 376 mls (4.37 mols) 40% aqueous methylamine solution at 15° C. in a 1 liter flask. The temperature was maintained below 25° C. during addition. After half an hour the bath was removed and the reaction stirred for 3 hours at ambient temperature. The solvent was removed under vacuum with a 50° C. bath to an end volume of 310 mls. The residue was then basilled with 50 g 10% NaOH to pH 12 and extracted into methylene chloride (2×160 mls). The combined organics were then washed with 1×150 g of 20% ammonium chloride followed by 1×90 g of 20% ammonium chloride. The combined aqueous washes were then back extracted with 150 mls methylene chloride. The combined product methylene chloride layers were then extracted with 100 g of a solution of 25 g conc. HCl and 75 g water. This acidic product solution was then washed with 135 mls methylene chloride. Next the acidic product solution was cooled, then neutralized with 100 g 20% NaOH solution. The product was extracted from this mixture with methylene chloride (2×135 mls). The solvent was removed under vacuum to afford the desired product as an amber oil. (yield approx. 28 grams)

EXAMPLE 27C

N-(N-Methyl-N-((2-isopropyl-4-thiazolyl)methyl)amino)carbonyl)-L-valine Methyl Ester Into a 500 ml 3-neck round bottom flask equipped with mechanical stirrer, nitrogen atmosphere, thermocouple, heating mantle and condensor was charged the product of Example 27B (28.1 g, 0.165 mols), phenoxycarbonyl-(L)-valine (41.5 g, 0.165 mol) and 155 ml toluene. This solution was warmed to reflux (110° C.) and stirred for three hours, then cooled to 20°±5° C. and washed with 2×69 ml 10% citric acid followed by 1×69 ml water, 1×116 mls 4% sodium hydroxide, 1×58 ml 4% sodium hydroxide and finally 1×58 ml water. The organic product solution was then treated with 3 grams of activated carbon at reflux for 15 minutes, filtered through infusorial earth to remove carbon, and the carbon/infusorial earth cake was washed with 25 ml hot toluene. Next the solvent was removed to afford a brown oil which solidifed upon cooling. This brown solid was dissolved with warming in 31 ml EtOAc and 257 ml heptane at 60°±5° C. This solution was slowly cooled to 25° C., stirred 12 hours, cooled further to 0° C., and stirred 3 hours. The crystals were collected by filtration and washed with 50 ml 1:9 EtOAc/Heptane. The solid was dried in a 50° C. vacuum oven for 12 hours to afford 41.5 grams of the desired product as a tan-colored solid (76.9%).

EXAMPLE 27D

N-((N-Methyl-N-((2-isopropyl-4-thiazolyl)methyl)amino)carbonyl)-L-valine

To a one liter three neck flask was charged the product of Example 27C (50 g, 0.153 mol), lithium hydroxide monohydrate (13 g, 0.310 mol), 200 ml THF and 190 ml water. This hazy solution was stirred for 2 hours. The reaction was quenched with a solution of conc. HCl (32.4 g, 0.329 mol) in 65 mL water, the THF was removed under vacuum and the product extracted into methylene chloride (3×210 ml). (NOTE: If necessary, the pH of the aqueous layer should be adjusted to maintain pH 1–4 during the extractions.) The combined organics were then dried with 50 g sodium sulfate, filtered with a 150 ml methylene chloride rinse of the sodium sulfate, and the solvent was removed under vacuum. The product was dissolved in 450 ml THF and again the solvent was removed. Next the product was dissolved in 475 ml THF containing 0.12 g butylated hydroxytoluene (BHT) for storage. If desired, the solvent can be removed under vacuum and the residual syrup dried in a vacuum oven at 55° C. to provide a glassy solid.

The above process for the preparation of compound III is disclosed in PCT Patent Application No. WO94/14436, published Jul. 7, 1994, which is hereby incorporated herein by reference.

Protocol For Oral Bioavailability Studies

Protocol A (solid dosage forms)

Dogs (beagle dogs, mixed sexes, weighing 7–14 kg) were fasted overnight prior to dosing, but were permitted water ad libitum. Each dog received a 0.5 mg/kg subcutaneous dose of histamine approximately 30 minutes prior to dosing. Each dog received a single solid dosage form corresponding to a 5 mg/kg dose of the drug. The dose was followed by approximately 10 milliliters of water. Blood samples were obtained from each animal prior to dosing at 0.25, 0.5, 1.0, 1.5, 2, 3, 4, 6, 8, 10 and 12 hours after drug administration. The plasma was separated from the red cells by centrifugation and frozen (–30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each capsule or capsule composition was evaluated in a group containing six dogs; the values reported are averages for each group of dogs. The average bioavailability data for the compositions of the Examples is shown in Table 1.

Protocol B (liquid dosage forms)

Dogs (beagle dogs, mixed sexes, weighing 7–14 kg) were fasted overnight prior to dosing, but were permitted water ad libitum. Each dog received a 0.5 mg/kg subcutaneous dose of histamine approximately 30 minutes prior to dosing. A 5 mg/kg dose, measured in a disposable syringe, was placed in the back of the throat of each animal. The dose was followed by approximately 10 milliliters of water. Blood samples were obtained from each animal prior to dosing at 0.25, 0.5, 1.0, 1.5, 2, 3, 4, 6, 8, 10 and 12 hours after drug administration. The plasma was separated from the red cells by centrifugation and frozen (–30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each liquid composition was evaluated in a group containing six dogs; the values reported are averages for each group of dogs. The average bioavailability data for the compositions of the Examples is shown in Table 1.

Protocol C (liquid dosage form followed by milk)

The animals were selected and pretreated with histamine as described in Protocol B above. The liquid dosage form (5 mg/kg dose), measured in a plastic syringe, was instilled into the back of the throat of each animal. A 10 mL aliquot of milk was also administered into the back of the throat of each dog. The liquid dosage form/milk combination was chased with an additional aliquot of water as described in Protocol B above. The sampling times, sample preparation and data analysis were as described in Protocol B.

Protocol D (liquid dosage form with milk)

The animals were selected and pretreated with histamine as described in Protocol B above. The liquid dosage form (5 mg/kg dose) was diluted ten fold with milk. The diluted dosage was measured in a plastic syringe and instilled into the back of the throat of each animal. The liquid dosage form was chased with an additional aliquot of water as described in Protocol B above. The sampling times, sample preparation and data analysis were as described in Protocol B.

TABLE 1

| Example No. | Mean % Bioavailability | Protocol |
| --- | --- | --- |
| Example 1 | 0.0 | A |
| Example 2 | 0.0 | A |
| Example 3 | 2.5 | A |
| Example 4 | 37.4 | B |
| Example 5 | 56.7 | D |
| Example 6 | 72.7 | B |
| Example 7 | 42.1 | C |
| Example 8 | 62.0 | D |
| Example 9 | 53.7 | D |
| Example 10 | 78.9 | C |
| Example 11 | 100.0 | C |
| Example 12 | 58.3 | B |
| Example 13 | 89.7 | C |
| Example 14 | 65.1 | C |
| Example 16 | 87.2 | C |
| Example 17 | 78.2 | C |
| Example 18 | 66.4 | C |
| Example 19 | 100.0 | C |

This data indicates that solution formulations provided significantly better bioavailability than non-formulated compound III.

Compounds I, II and III are inhibitors of HIV-1 and HIV-2-protease. They are useful for inhibiting an HIV infection and treating AIDS in humans. Total daily dose of compound I, II or III administered to a human in single or divided doses may be in amounts, for example, from 0.001 to 1000 mg/kg body weight daily but more usually 0.1 to 50 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

The foregoing is merely illustrative of the invention and is not intended to limit the invention to the disclosed compounds, methods and compositions. Variations and changes which are obvious to one skilled in the art are intended to be within the scope and nature of the invention which are defined in the appended claims.

What is claimed is:

1. A pharmaceutical composition comprising a solution of an HIV protease inhibiting compound in a pharmaceutically acceptable organic solvent comprising a mixture of (1) (a) a solvent selected from propylene glycol and polyethylene glycol or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy)ethanol or (c) a mixture thereof and (2) ethanol or propylene glycol wherein the HIV protease Inhibiting compound is selected from the group consisting of:

N-(2(R)-hydroxy-1(S)-Indanyl)-2(R)-phenylmethyl-4(S)-hydroxy-5-(1-(4-(3-pyridylmethyl)-2(S)-N'-(t-butylcarboxamido)-piperazinyl))-pentaneamide: N-tert-butyl-decahydro-2-(2(R)-hydroxy-4-phenyl-3(S)-((N-(2-quinolylcarbonyl)-L-asparaginyl)amino] butyl)-(4aS,8aS)-isoquinoline-3(S)-carboxamide; (1S-(1R*(R*),2S*)}-$N^1$(3-((((1,1-dimethylethyl)amino)carbonyl)(2-methylpropyl)amino)-2hydroxy-1-(phenylmethyl)propyl)-2-((2-quinolinylcarbonyl)amino)-butanediamide; and

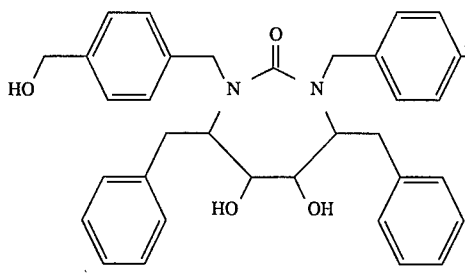
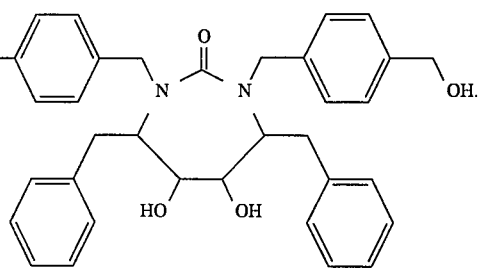

2. The composition of claim 1 comprising a solution of the HIV protease inhibiting compound in a pharmaceutically acceptable organic solvent comprising a mixture of (1) propylene glycol or polyoxyethyleneglycerol triricinoleate or a mixture thereof and (2) ethanol.

3. The composition of claim 1 further comprising a pharmaceutically acceptable acid.

4. The composition of claim 1 further comprising water.

5. The composition of claim 1 further comprising one or more additives independently selected from pharmaceutically acceptable organic solvents, pharmaceutically acceptable oils, pharmaceutically acceptable sweetening agents, pharmaceutically acceptable flavoring agents, pharmaceutically acceptable surfactants and antioxidants.

6. The composition of claim 1 wherein the HIV protease inhibiting compound is N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide.

7. The composition of claim 1 wherein the HIV protease inhibiting compound is N-tert-butyl-decahydro-2-(2(R)-hydroxy-4-phenyl-3(S)-((N-(2-quinolylcarbonyl)-L-asparaginyl)amino]butyl)-(4aS,8aS)-isoquinoline-3(S)-carboxamide.

8. The composition of claim 1 wherein the HIV protease inhibiting compound is (1S-(1R*(R*),2S*)}-N¹(3-((((1,1-dimethylethyl)amino)carbonyl)(2-methylpropyl)amino)-2-hydroxy-1-(phenylmethyl)propyl)-2-((2-quinolinylcarbonyl)amino)-butanediamide.

9. The composition of claim 1 wherein the HIV protease inhibiting compound is 10. A pharmaceutical composition comprising a solution of a compound of the formula:

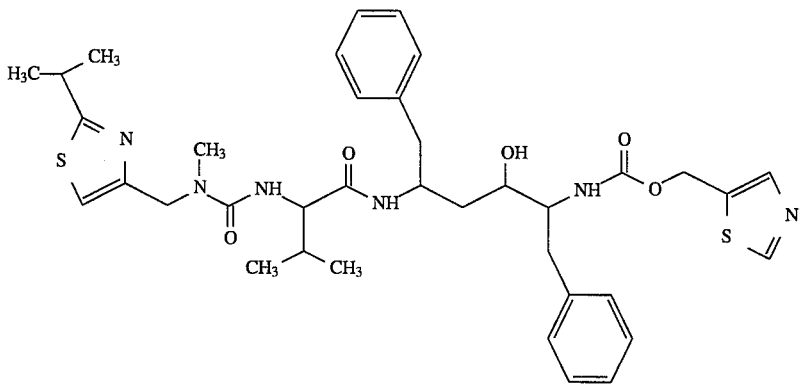

in a pharmaceutically acceptable organic solvent comprising a mixture of (1) (a) a solvent selected from propylene glycol and polyethylene glycol or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy)ethanol or (c) a mixture thereof and (2) ethanol or propylene glycol.

11. The composition of claim 10 comprising a solution of a compound of the formula:

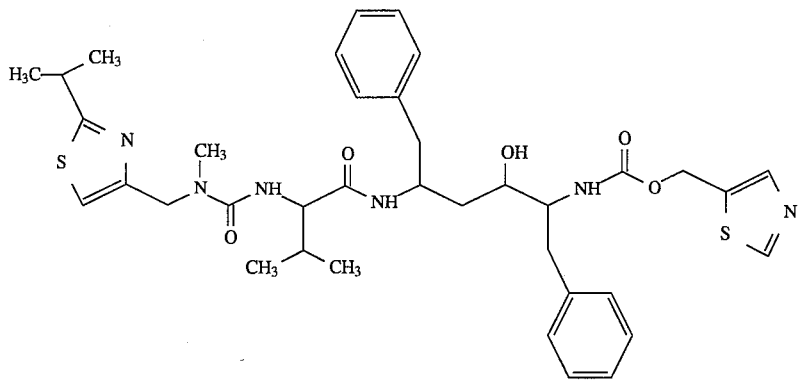

in a pharmaceutically acceptable organic solvent comprising a mixture of (1) propylene glycol or polyoxyethyleneglycerol triricinoleate or a mixture thereof and (2) ethanol.

12. The composition of claim 10 further comprising a pharmaceutically acceptable acid or a mixture of pharmaceutically acceptable acids.

13. The composition of claim 10 further comprising water.

14. The composition of claim 10 further comprising one or more additives independently selected from pharmaceutically acceptable organic solvents, pharmaceutically acceptable oils, pharmaceutically acceptable sweetening agents, pharmaceutically acceptable flavoring agents, pharmaceutically acceptable surfactants and antioxidants.

15. The composition of claim 10 comprising a solution of from about 1% to about 15% by weight of the total solution of a compound of the formula:

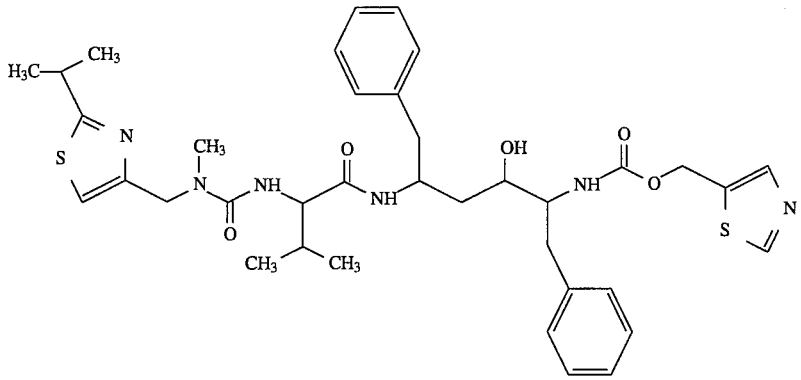

in a pharmaceutically acceptable organic solvent comprising a mixture of (1) propylene glycol in the amount of from about 10% to about 50% by weight of the total solution or polyoxyethyleneglycerol triricinoleate in the amount of from about 5% to about 35% by weight of the total solution or a mixture thereof and (2) ethanol in the amount of from about 5% to about 45% by weight of the total solution.

16. The composition of claim 15 further comprising a pharmaceutically acceptable acid in the amount of from about 0.2% to about 16% by weight of total solution.

17. The composition of claim 15 comprising a solution of from about 1% to about 15% by weight of the total solution of (2S,3S,5S)-5-(N-(N-((N-Methyl-N-((2-isopropyl-4-thiazolyl)methyl)-amino)carbonyl)valinyl)amino-2-(N-((5-thiazolyl)methoxycarbonyl)amino)-1,6-diphenyl-3-hydroxyhexane in a pharmaceutically acceptable organic solvent comprising a mixture of (1) propylene glycol in the amount of from about 10% to about 50% by weight of the total solution or polyoxyethyleneglycerol triricinoleate in the amount of from about 5% to about 35% by weight of the total solution or a mixture thereof and (2) ethanol in the amount of from about 5% to about 45% by weight of the total solution.

18. The composition of claim 17 further comprising a pharmaceutically acceptable acid in the amount of from about 0.2% to about 16% by weight of total solution.

19. The composition of claim 18 wherein the pharmaceutically acceptable acid is citric acid.

20. The composition of claim 19 comprising a solution of about 5% by weight of the total solution of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane and about 4% by weight of the total solution of citric acid in a pharmaceutically acceptable organic solvent comprising a mixture of (1) propylene glycol in the amount of about 42% by weight of the total solution, (2) ethanol in the amount of about 32% by weight of the total solution and (3) water in the amount of about 17% by weight of the total solution.

21. The composition of claim 19 comprising a solution of about 12% by weight of the total solution of (2S,3S,5S)-5-(N-(N-((N-Methyl-N-((2-isopropyl-4-thiazolyl)methyl)amino)carbonyl)valinyl)amino-2-(N-((5-thiazolyl)methoxycarbonyl)amino)-1,6-diphenyl-3-hydroxyhexane and from about 3% to about 4% by weight of the total solution of citric acid in a pharmaceutically acceptable organic solvent comprising a mixture of (1) propylene glycol in the amount of about 32% by weight of the total solution, (2) ethanol in the amount of about 37% by weight of the total solution and (3) water in the amount of about 15% by weight of the total solution.

22. The composition of claim 19 comprising a solution of about 5% by weight of the total solution of (2S,3S,5S)-5-(N-(N-((N-Methyl-N-((2-isopropyl-4-thiazolyl)methyl)amino)carbonyl)valinyl)amino-2-(N-((5-thiazolyl)methoxycarbonyl)amino)-1,6-diphenyl-3-hydroxyhexane and from about 5% to about 6% by weight of the total solution of citric acid in a pharmaceutically acceptable organic solvent comprising a mixture of (1) propylene glycol in the amount of from about 44% to about 45% by weight of the total solution, (2) ethanol in the amount of about 24% by weight of the total solution and (3) polyoxyethyleneglycerol triricinoleate in the amount of about 20% by weight of the total solution.

23. The composition of claim 19 comprising a solution of about 10% by weight of the total solution of (2S,3S,5S)-5-(N-(N-((N-Methyl-N-((2-isopropyl-4-thiazolyl)methyl)amino)carbonyl)valinyl)amino- 2-(N-((5-thiazolyl)methoxycarbonyl)amino)-1,6-diphenyl-3-hydroxyhexane and from about 5% to about 6% by weight of the total solution of citric acid in a pharmaceutically acceptable organic solvent comprising a mixture of (1) propylene glycol in the amount of from about 39% to about 40% by weight of the total solution, (2) ethanol in the amount of about 24% by weight of the total solution and (3) polyoxyethyleneglycerol triricinoleate in the amount of about 20% by weight of the total solution.

24. The composition of claim 19 comprising a solution of from about 2% to about 3% by weight of the total solution of (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane and about 4% by weight of the total solution of citric acid in a pharmaceutically acceptable organic solvent comprising a mixture of (1) propylene glycol in the amount of about 43% by weight of the total solution, (2) ethanol in the amount of about 33% by weight of the total solution and (3) water in the amount of about 17% by weight of the total solution.

25. The composition of claim 19 comprising a solution of about 5% by weight of the total solution of (2S,3S,5S)-5-(N-(N-((N-Methyl-N-((2-isopropyl-4-thiazolyl)methyl)amino)carbonyl)valinyl)amino-2-(N-((5-thiazolyl)methoxycarbonyl)amino)-1,6-diphenyl-3-hydroxyhexane and from about 0.3 to about 0.4% by weight of the total solution of citric acid in a pharmaceutically acceptable organic solvent comprising a mixture of (1) propylene glycol in the amount of about 36% by weight of the total solution, (2) ethanol in the amount of about 36% by weight of the total solution and (3) water in the amount of about 19% by weight of the total solution.

26. The composition of claim 19 comprising a solution of about 8% by weight of the total solution of (2S,3S,5S)-5-(N-(N-((N-Methyl-N-((2-isopropyl-4-thiazolyl)methyl)amino)carbonyl)valinyl)amino-2-(N-((5-thiazolyl)methoxycarbonyl)amino)-1,6-diphenyl-3-hydroxyhexane and from about 0.3 to about 0.4% by weight of the total solution of citric acid in a pharmaceutically acceptable organic solvent comprising a mixture of (1) propyleneglycol in the amount of about 35% by weight of the total solution, (2) ethanol in the amount of about 35% by weight of the total solution and (3) water in the amount of about 18% by weight of the total solution.

27. The composition of claim 19 comprising a solution of from about 7% to about 8% by weight of the total solution of (2S,3S,5S)-5-(N-(N-((N-MethyI-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane and about 0.5% by weight of the total solution of citric acid in a pharmaceutically acceptable organic solvent comprising a mixture of (1) propylene glycol in the amount of from about 45% to about 46% by weight of the total solution, (2) ethanol in the amount of about 21% by weight of the total solution and (3) polyoxyethyleneglycerol triricinoleate in the amount of from about 24% to about 25% by weight of the total solution.

28. The composition of claim 19 comprising a solution of from about 7% to about 8% by weight of the total solution of (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane and from about 0.2% to about 0.3% by weight of the total solution of citric acid in a pharmaceutically acceptable organic solvent comprising a mixture of (1) propylene glycol in the amount of from about 31% to about 32% by weight of the total solution, (2) ethanol in the amount of about 32% by weight of the total solution, (3) polyoxyethyleneglycerol triricinoleate in the amount of from about 10% to about 11% by weight of the total solution and (4) water in the amount of from about 14% to about 15% by weight of the total solution.

* * * * *

UNITED STATES PATENT AND TRADEMARK OFFICE
CERTIFICATE OF CORRECTION

PATENT NO. : 5,484,801
DATED : January 16, 1996
INVENTOR(S) : L. A. Al-Razzak, et al.

It is certified that error appears in the above-indentified patent and that said Letters Patent is hereby corrected as shown below:

Column 16, line 3, change "$R_f=0.25$" to --$R_f$-0.25--.

Column 16, line 41, change "amino-1,6" to --amino)1,6--.

Column 16, line 64, change "7.07(b d,J" to --7.07(brd,J--.

Column 20, line 63, change "volume/n vacuo," to --volume in vacuo,--.

Column 24, line 30, change "dissolve the the crude" to --dissolve the crude--.

Column 24, line 40, change "< 45° C." to --≤ 45° C.--.

Column 24, line 49, change "70° C." to --~ 70° C.--.

Column 25, line 67, change "rotary evaporate at 50° C." to --rotary evaporator at 50° C.--.

Column 27, line 63, change "basilled with" to --basified with--.

UNITED STATES PATENT AND TRADEMARK OFFICE
CERTIFICATE OF CORRECTION

PATENT NO. : 5,484,801  Page 2 of 2
DATED : January 16, 1996
INVENTOR(S) : L. A. Al-Razzak, et al.

It is certified that error appears in the above-indentified patent and that said Letters Patent is hereby corrected as shown below:

Column 35, line 10, change "amino-2" to --amino)-2--.

Column 35, line 23, change "amino-2" to --amino)-2--.

Column 35, line 48, change "valinyl)amino-2" to --valinyl)amino)-2--.

Column 36, line 15, change "propyleneglycol" to --propylene glycol--.

Column 34, line 65, change "amino-2" to --amino)-2--.

Signed and Sealed this

Third Day of December, 1996

Attest:

BRUCE LEHMAN

*Attesting Officer*  *Commissioner of Patents and Trademarks*